US009585893B2

(12) United States Patent
Amselem

(10) Patent No.: US 9,585,893 B2
(45) Date of Patent: Mar. 7, 2017

(54) FLUMAZENIL COMPLEXES, COMPOSITIONS COMPRISING SAME AND USES THEREOF

(71) Applicant: COERULEUS LTD., Katzrin, IL (US)

(72) Inventor: Shimon Amselem, Rehovot (IL)

(73) Assignee: COERULEUS LTD., Katzrin (IL)

( * ) Notice: Subject to any disclaimer, the term of this patent is extended or adjusted under 35 U.S.C. 154(b) by 273 days.

(21) Appl. No.: 13/974,760

(22) Filed: Aug. 23, 2013

(65) Prior Publication Data

US 2013/0345202 A1 Dec. 26, 2013

Related U.S. Application Data

(63) Continuation of application No. PCT/IL2012/050060, filed on Feb. 23, 2012.

(60) Provisional application No. 61/445,559, filed on Feb. 23, 2011.

(51) Int. Cl.
| A61K 31/55 | (2006.01) |
| A01N 43/62 | (2006.01) |
| A61K 31/5517 | (2006.01) |
| A61K 31/455 | (2006.01) |
| A61K 45/06 | (2006.01) |
| A61K 47/10 | (2006.01) |
| A61K 47/18 | (2006.01) |
| A61K 47/40 | (2006.01) |
| C07D 487/04 | (2006.01) |
| A61K 9/00 | (2006.01) |

(52) U.S. Cl.
CPC ........ *A61K 31/5517* (2013.01); *A61K 9/0056* (2013.01); *A61K 31/455* (2013.01); *A61K 45/06* (2013.01); *A61K 47/10* (2013.01); *A61K 47/18* (2013.01); *A61K 47/40* (2013.01); *C07D 487/04* (2013.01)

(58) Field of Classification Search
CPC .. A61K 31/455; A61K 31/5517; A61K 45/06; A61K 47/10; A61K 47/18; A61K 47/40; A61K 9/0056; C07D 487/04
USPC .......................................... 514/220; 540/498
See application file for complete search history.

(56) References Cited

U.S. PATENT DOCUMENTS

| 3,943,137 | A | 3/1976 | Higuchi et al. |
| 4,316,839 | A | 2/1982 | Gerecke et al. |
| 5,073,543 | A | 12/1991 | Marshall et al. |
| 5,120,548 | A | 6/1992 | McClelland et al. |
| 5,570,698 | A | 11/1996 | Liang et al. |
| 5,639,476 | A | 6/1997 | Oshlack et al. |
| 5,682,144 | A | 10/1997 | Mannik |
| 5,689,241 | A | 11/1997 | Clarke, Sr. et al. |
| 5,733,566 | A | 3/1998 | Lewis |
| 5,811,547 | A | 9/1998 | Nakamichi et al. |
| 6,087,353 | A | 7/2000 | Stewart et al. |
| 6,573,237 | B2 * | 6/2003 | Rinella, Jr. ............... 514/9.9 |
| 7,056,934 | B2 | 6/2006 | Bunnage et al. |
| 7,153,870 | B2 | 12/2006 | Mathias |
| 2001/0053776 | A1 | 12/2001 | Crawforth et al. |
| 2002/0099013 | A1 | 7/2002 | Piccariello et al. |
| 2002/0142050 | A1 | 10/2002 | Straub et al. |
| 2003/0077227 | A1 | 4/2003 | Dugger, III |
| 2003/0082107 | A1 | 5/2003 | Dugger, III |
| 2004/0186075 | A1 | 9/2004 | Loftsson et al. |
| 2005/0137141 | A1 | 6/2005 | Hilfinger |
| 2005/0233000 | A1 | 10/2005 | Figueroa et al. |
| 2005/0238697 | A1 | 10/2005 | Chinea et al. |
| 2005/0267100 | A1 | 12/2005 | Elliott et al. |
| 2006/0024365 | A1 | 2/2006 | Vaya et al. |
| 2006/0051412 | A1 | 3/2006 | Petereit et al. |
| 2006/0167068 | A1 | 7/2006 | Feuerstein et al. |
| 2007/0020336 | A1 | 1/2007 | Loftsson et al. |
| 2007/0265193 | A1 | 11/2007 | Elliott et al. |
| 2009/0130216 | A1 | 5/2009 | Cartt et al. |
| 2009/0270373 | A1 | 10/2009 | Rao et al. |
| 2010/0130479 | A1 | 5/2010 | Cook et al. |
| 2011/0028418 | A1 | 2/2011 | Parker et al. |
| 2011/0160543 | A1 | 6/2011 | Parsey et al. |
| 2011/0256070 | A1 | 10/2011 | Martin et al. |

FOREIGN PATENT DOCUMENTS

| CN | 101322688 A | 12/2008 |
| DE | 10304403 A1 | 8/2004 |
| EP | 1374952 A1 | 1/2004 |
| EP | 1378267 A1 | 1/2004 |
| EP | 2065038 A1 | 6/2009 |
| WO | 9625948 A1 | 8/1996 |
| WO | 9942111 A1 | 8/1999 |
| WO | 9961014 A2 | 12/1999 |

(Continued)

OTHER PUBLICATIONS

Amrein, Pharmacology of Dormicum® (midazolam) and Anexate® (flumazenil), Acta Anaesthesiol Scand, 34, Supplementum 92: 6-15, 1990.*
Ammar, Effect of aromatic hydrotropes on the solubility of oxamniquine. Part 2: Effect of nicotinamide and sodium salts of benzoic, naphthoic, nicotinic and isonicotinic acids, Pharmazie, 51(7): 490-493, 1996.*
Ammar, Effect of aromatic hydrotropes on the solubility of carbamazepine. Part II: Effect of nicotinamide, sodium salts of benzoic, naphthoic and nicotinic acids, Egyptian Journal of Pharmaceutical Sciences, 35(1-6): 209-223, 1994.*
Ammar, Effect of aromatic hydrotropes on the solubility of phenacetin. Part 2: Effect of nicotinamide and sodium salts of benzoic, naphthoic and nicotinic acids, Pharmazie, 48(11):845-8, 1993.*

(Continued)

*Primary Examiner* — My-Chau T Tran
(74) *Attorney, Agent, or Firm* — The Roy Gross Law Firm, LLC; Roy Gross

(57) ABSTRACT

Soluble complexes of flumazenil, methods for the preparation thereof, pharmaceutical compositions including same and use of the compositions for alleviating or counteracting the various types of hypersomnia, drowsiness, residual effects associated with the administration of sleep/hypnotic drugs, alcohol intoxication or hepatic encephalopathy.

20 Claims, 3 Drawing Sheets

(56) References Cited

FOREIGN PATENT DOCUMENTS

| WO | 0072827 A2 | 12/2000 |
| WO | 0205851 A2 | 1/2002 |
| WO | 0234237 A1 | 5/2002 |
| WO | 02056964 A1 | 7/2002 |
| WO | 03013538 A1 | 2/2003 |
| WO | 03034980 A2 | 5/2003 |
| WO | 2004016265 A1 | 2/2004 |
| WO | 2004/089313 | 10/2004 |
| WO | 2005063248 A1 | 7/2005 |
| WO | 2005063297 A2 | 7/2005 |
| WO | 2006088894 A2 | 8/2006 |
| WO | 2007009691 A2 | 1/2007 |
| WO | 2008024490 A2 | 2/2008 |
| WO | 2008071665 A1 | 6/2008 |
| WO | 2008128116 A1 | 10/2008 |
| WO | 2009068668 A1 | 6/2009 |
| WO | 2009114740 A2 | 9/2009 |
| WO | WO 2009/114740 A2 * | 9/2009 ......... A61K 31/5517 |
| WO | 2009124755 A1 | 10/2009 |
| WO | 2011073985 A1 | 6/2011 |
| WO | 2011152926 A1 | 12/2011 |
| WO | 2012114342 A1 | 8/2012 |
| WO | 2012135536 A1 | 10/2012 |

OTHER PUBLICATIONS

Shokri et al., The effect of surfactants on the skin penetration of diazepam, International Journal of Pharmaceutics 228:99-107, 2001.*

Sinha, Permeation Enhancers for Transdermal Drug Delivery, Drug Development and Industrial Pharmacy, 26(11), 1131-1140, 2000.*

Fonti et al., (1999) "99mTc-monoclonal antibody radiolabeled via hydrazino nicotinamide derivative for imaging disialoganglioside G(D2)-positive tumors"; Nucl Med Biol 26(6): 681-686.

Johns MW (1991) "A new method for measuring daytime sleepiness: the Epworth sleepiness scale" Sleep 14 (6): 540-545 (1 page abstract only).

Als-Nielsen et al., (2004) "Benzodiazepine receptor antagonists for hepatic encephalopathy"; Cochrane Database Syst Rev (2): CD002798. DOI: 10.1002/14651858.CD002798.pub2; 41 pages.

Kuramochia et al., (2005) "Discovery of an N-(2-aminopyridin-4-ylmethyl)nicotinamide derivative: a potent and orally bioavailable NCX inhibitor"; Bioorg Med Chem 13(12): 4022-4036.

Bond (1998) "Drug-induced behavioural disinhibition"; CNS Drugs 9(1): 41•57.

Avallone et al., (1998) "Endogenous benzodiazepine-like compounds and diazepam binding inhibitor in serum of patients with liver cirrhosis with and without overt encephalopathy"; Gut 42: 861-867.

Rizwan et al., (2009) "Enhanced transdermal drug delivery techniques: an extensive review of patents"; Recent Pat Drug Deliv Formul 3(2): 105-124.

Patat et al., (1994) "Flumazenil antagonizes the central effects of zolpidem, an imidazopyridine hypnotic"; Clin Pharmacol Ther 56(4): 430-436.

International Search Report and Written Opinion of the International Searching Authority Application No. PCT/IL2012/050060 Completed: Jul. 5, 2012; Mailing Date: Jul. 16, 2012 7 pages.

Baraldi et al., (2009) "Natural endogenous ligands for benzodiazepine receptors in hepatic encephalopathy"; Metab Brain Dis 24: 81-93.

"A new Method for Measuring Daytime Sleepiness: The Epworth Sleepiness Scale" (Johns MW (1991) Sleep 14(6):540-5).

The Development and Use of the Stanford Sleepiness Scale (SSS) (Hoddes et al (1972) Psychophysiology 9:150 ; Sleep Study Abstract; 1 page.

Goulenok et al: "Flumazenil vs. placebo in hepatic encephalopathy in patients with cirrhosis: a meta-analysis", Alimentary Pharmacology Therapeutics; vol. 16, Issue 3, pp. 361-372. Oct. 11, 2001.

Miroshnyk et al.: "Pharmaceutical co-crystals-an opportunity for drug product enhancement", Expert Opinion Drug Delivery 6(4), pp. 333-341.

Saadi et al.: "Pharmacokinetics and Safety of Sublingual Flumazenil (CRLS035) in Healthy Adults (Potential Therapy for Hepatic Encephalopathy)", Journal of Pharmacogenomics Pharmacoproteomics, vol. 5, Issue 4, pp. 1-7.

Rajewski et al.: "Preliminary safety evaluation of parenterally administered sulfoalkyl ether beta-cyclodextrin derivatives", Journal of Pharmaceutical Sciences, vol. 84, No. 8, pp. 927-932.

Buck et al.: "Reversal of Alcohol Dependence and Tolerance by a Single Administration of Flumazenil", The Journal of Pharmacology and Experimental Therapeutics, vol. 257, No. 3, pp. 984-989. Denver, CO, Feb. 22, 1991.

Rasool et al: "Solubility enhancement of some water-insoluble drugs in the presence of nicotinamide and related compounds", Journal of Pharmaceutical Sciences, vol. 80, No. 4, pp. 387-393.

Sanghvi et al.: "Stacking complexation by nicotinamide: A useful way of enhancing drug solubility", International Journal of Pharmaceutics 336, pp. 35-41.

Bold et al., (1985) Central effects of nicotinamide and inosine which are not mediated through benzodiazepine receptors. Br J Pharmacol 84(3): 689-96.

Mohler et al., (1979) Nicotinamide is a brain constituent with benzodiazepine-like actions. Nature 278(5704): 563-5.

Peiying Wu et al., (2005) The progress of study on a method for solubilizing insoluble drugs. Chinese Traditional Patent Medicine 27(9): 10-13 Partial translation.

Yousheng Chen et al, (2008) Research on how to improve solubility of water-insoluable drugs. Strait Pharmaceutical Journal 20(7): 25-27 abstract.

* cited by examiner

FLUMAZENIL COMPLEXES, COMPOSITIONS COMPRISING SAME AND USES THEREOF

FIELD OF THE INVENTION

The present invention provides soluble complexes of flumazenil, methods for the preparation thereof, pharmaceutical compositions comprising same and use of said compositions for alleviating or counteracting the various types of hypersomnia, drowsiness, residual effects associated with the administration of sleep/hypnotic drugs, sedation, alcohol intoxication and hepatic encephalopathy.

BACKGROUND OF THE INVENTION

Flumazenil (chemically named ethyl 8-fluoro-5,6-dihydro-5-methyl-6-oxo-4H-imidazo[1,5-a][1,4]benzodiazepine-3-carboxylate), also known as, Ro 15-1788, Anexate™, Lanexat™, Mazicon™ and Romazicon™, was initially disclosed in U.S. Pat. No. 4,316,839. Flumazenil is an imidazobenzodiazepine having high affinity for the $GABA_A$/benzodiazepine-receptor complex, the specific binding site of benzodiazepines. As flumazenil is a competitive inhibitor of benzodiazepines, it is used for reversing benzodiazepine-induced sedation and anesthesia following therapeutic or diagnostic procedures (e.g. WO 2009/114740). Flumazenil is also known to reverse the effect of non-benzodiazepine drugs, such as the imidazopyridine hypnotic zolpidem (e.g. Patat et al., Clin Pharmacol Ther., 1994, 56(4):430-6). Flumazenil antagonizes the central effects of zolpidem, an imidazopyridine hypontic) (Bond A J, 1998, CNS Drugs, 9(1): 41-57). Flumazenil is also effective in treating hepatic encephalopathy (Als-Nielsen B et al. Cochrane Database of Systematic Reviews 2004, Issue 2. Art. No.: CD002798. DOI: 10.1002/14651858.CD002798.pub2). The aforementioned therapeutic effects were achieved by intravenous administration of flumazenil in a liquid formulation.

A liquid formulation of flumazenil (Romazicon®) is currently approved for reversing the sedative effects of benzodiazepines. Due to the limited solubility of flumazenil, the Romazicon® liquid formulation contains only 0.01% flumazenil. Poor water solubility frequently correlates with low drug absorption and bioavailability, and limits the amount of drug that can be administered in a pharmaceutical composition.

The use of hydrotopes, such as nicotinamide, for complexation with insoluble compounds in order to improve their solubility is known, for example, U.S. Pat. No. 6,087,353.

There remains an unmet need to formulate flumazenil derivatives that are highly soluble and thereby suitable for the preparation of highly concentrated flumazenil formulations.

SUMMARY OF THE INVENTION

The present invention is directed to pharmaceutically acceptable complexes of flumazenil, comprising flumazenil and a complexation agent. The flumazenil complexes of the invention are highly soluble while maintaining the therapeutic activity known for flumazenil, namely, ameliorating or inhibiting any type of hypersomnia and drowsiness, including endogenous hypersomnia associated with GABA hyper-activation or exogenic hypersomnia e,g, residual hypersomnia associated with the administration of sleep/hypnotic drugs and ameliorating or inhibiting alcohol intoxication, or treating hepatic encephalopathy or any other disease or disorder associated with GABA related sedation or hypnotics. Having a significantly higher solubility of flumazenil, the flumazenil complexes of the invention offer a pronounced advantage over flumazenil compositions currently known in the art. Moreover, the flumazenil complexes of invention are advantageous for the preparation of formulations suitable for self-administration, such as, sublingual administration, thereby avoiding the involvement of professional care takers and the need of admitting to a health center.

The present invention is based in part on the unexpected discovery that flumazenil complexes are more soluble than flumazenil alone. Accordingly, these compounds are suitable for the preparation of highly concentrated pharmaceutical compositions of flumazenil. This enables administration of higher doses of flumazenil (per volume) than currently available. Typically, the concentration of flumazenil in the form of the flumazenil complexes of the invention is within the range of about 0.4 to 2%. This concentration is much higher than the concentration of flumazenil in commercially available formulations. In fact, the concentration of flumazenil in the pharmaceutical compositions of the invention is higher by more than two orders of magnitude from the concentration of flumazenil in the commercially available formulations. Highly concentrated flumazenil compositions are particularly advantageous in view of the maximal recommended daily dose approved for flumazenil solution (for example, Romazicon®), which is 3 mg. As the concentration of flumazenil in the commercial solution is only 0.01%, a dose of 3 mg requires administration of a large volume of the flumazenil solution, as high as 30 ml. The present invention overcomes this deficiency by providing concentrated formulations that can be administered in lower volumes thus improving patient compliance. Administering highly concentrated formulations of flumazenil also enables applying more routes of delivery, specifically, sublingual, submucosal, intramuscular, transdermal or any parentral route of administration.

Sublingual administration of the formulations of the invention is of special advantage. Apart from being easy to administer, the sublingual route bypasses the first liver metabolism, absorbance of flumazenil is immediate, thereby fast response to therapy can be achieved.

Although being highly concentrated, the formulations of the invention are stable and no precipitation occurs during storage. The stability of the formulations of the invention renders them suitable for long periods of storage.

According to a first aspect, the present invention provides a complex of ethyl 8-fluoro-5,6-dihydro-5-methyl-6-oxo-4H-imidazo[1,5-a][1,4]benzodiazepine-3-carboxylate (flumazenil) or a salt thereof and a complexation agent or derivatives thereof, with the proviso that the complexation agent is other than cyclodextrin or meglumine.

According to another aspect, the present invention provides a complex of ethyl 8-fluoro-5,6-dihydro-5-methyl-6-oxo-4H-imidazo[1,5-a][1,4]benzodiazepine-3-carboxylate (flumazenil) or a salt thereof and an aromatic stacking complexation agent.

According to another embodiment, the stacking complexation agent is selected from the group consisting of: benzoic acid, benzoate, hydroxybenzoic acid, hydroxybenzoate, salicylic acid, salicylate, nicotinamide, nicotinic acid, nicotinate, gentisic acid, gentisate, ethanolamide, toluic acid (ortho, meta or para), toluate (ortho, meta or para), aminobenzoic acid, aminobenzoate, anthranilic acid, anthranilate, butylmonoglycolsulfate and resorcinol.

According to yet another embodiment, the stacking complexation agent is selected from the group consisting of: benzoic acid, sodium benzoate, potassium benzoate, hydroxybenzoic acid, sodium hydroxybenzoate, potassium hydroxybenzoate, salicylic acid, sodium salicylate, potassium salicylate, nicotinamide, nicotinic acid, sodium nicotinate, potassium nicotinate, gentisic acid, sodium gentisate, potassium gentisate, ethanolamide, sodium toluate, toluic acid, potassium toluate, aminobenzoic acid, sodium aminobenzoate, potassium aminobenzoate, anthranilic acid, sodium anthranilate, potassium anthranilate, sodium butylmonoglycolsulfate, potassium butylmonoglycolsulfate and resorcinol.

According to yet another embodiment, the stacking complexation agent is selected from the group consisting of: sodium benzoate, sodium hydroxybenzoate, sodium salicylate, nicotinamide, sodium nicotinate, sodium gentisate, gentisic acid ethanolamide, sodium toluate, sodium aminobenzoates, sodium anthranilate, sodium butylmonoglycolsulfate and resorcinol.

It is noted that the complexation agent of the flumazenil complex of the current invention may be any complexation agent known in the art other than cyclodextrin. However, the present invention contemplates compositions comprising the flumazenil complexes of the invention, and cyclodextrin as an additional excipient.

According to one embodiment, the complexation agent is nicotinamide or a derivative thereof. According to yet another embodiment, the nicotinamide derivative is selected from the group consisting of: 2-amino-nicotinamide derivatives, 5-phenyl-nicotinamide derivative and 6-substituted nicotinamide derivative.

According to yet another embodiment, the complexation agent:flumazenil ratio is in the range of 1:1 to 2:1.

According to another aspect, the present invention provides a flumazenil nicotinamide stacking complex.

According to yet another aspect, the present invention provides a pharmaceutical composition comprising the flumazenil complex and a pharmaceutical acceptable carrier.

According to yet another embodiment, the pharmaceutical composition is in a form selected from the group consisting of: a pill, tablet, lozenge, coated tablet, granule, capsule, hard or soft gelatin capsule, aqueous solution, alcoholic solution, oily solution, syrup, emulsion suspension pastille suppository, solution for injection or infusion, ointment, tincture, cream, lotion, powder, spray, transdermal therapeutic systems, nasal spray, buccal spray, aerosol mixture, microcapsule, implant, rod and plaster. Each possibility represents a separate embodiment of the present invention.

According to yet another embodiment, the pharmaceutical composition is in a form selected from the group consisting of: immediate release, delayed release, pulsatile release, continuous release and repetitive release. Each possibility represents a separate embodiment of the present invention.

According to yet another embodiment, the composition is in a solid dosage form. According to yet another embodiment, the composition is suitable for oral administration.

According to yet another embodiment, flumazenil concentration in the pharmaceutical composition is within the range of about 0.4 to 2% w/w. According to yet another embodiment, the concentration of flumazenil is within the range of about 0.5 to 1.8% w/w. According to certain embodiments, the concentration of flumazenil is within the range of about 0.6 to 1.5% w/w.

According to yet another embodiment, the pharmaceutical composition comprises flumazenil complex as an active ingredient, and a solubilizing agent selected from an alcohol, a glycol and a combination thereof. Each possibility represents a separate embodiment of the present invention.

According to yet another embodiment, the solubilizing agent comprises a combination of an alcohol and a glycol wherein the alcohol:glycol ratio is at least 1.5:1. According to yet another embodiment, the alcohol:glycol ratio is in the range of 1.5:1 to 5:1.

According to yet another embodiment, the solubilizing agent comprises a combination of an alcohol and a glycol wherein the concentration of the solubilizing agent is at least 40%. According to yet another embodiment, the solubilizing agent comprises a combination of an alcohol and a glycol wherein the concentration of the solubilizing agent is in the range of 40% to 60%. According to yet another embodiment, the solubilizing agent comprises ethanol and propylene glycol.

According to yet another embodiment, the pharmaceutical composition further comprises a buffering agent.

According to yet another embodiment, the pharmaceutical composition further comprises at least one agent selected from the group consisting of: a penetration enhancer, a surfactant and cyclodextrin, as an inclusion complexing agent. Each possibility represents a separate embodiment of the present invention.

According to yet another embodiment, the cyclodextrin is hydroxypropyl β-cyclodextrin (HPCD). The cyclodextrin is preferably formulated in a buffer having a pH from about 3 to about 6. In one particular embodiment, the cyclodextrin (e.g., HPCD) is formulated in a citric acid buffer having a pH of about 4.

According to yet another embodiment, the preservative is selected from the group consisting of benzyl alcohol, propylparaben, methylparaben and combinations thereof. In one embodiment, the preservative is benzyl alcohol. In another embodiment, the preservative is a combination of propylparaben and methylparaben. Each possibility represents a separate embodiment of the present invention.

According to yet another embodiment, the penetration enhancer is menthol.

According to yet another embodiment, the buffering agent is selected from the group consisting of: citric buffer, sodium chloride and combination thereof. Each possibility represents a separate embodiment of the present invention.

According to yet another embodiment, the surfactant is a cationic surfactant.

According to yet another embodiment, the surfactant is benzalkonium chloride.

According to yet another aspect, the present invention provides a method for treating a disease or disorder associated with binding of an agent to the GABA receptor, comprising administering to a patient in need thereof a pharmaceutical composition comprising as an active ingredient a flumazenil complex, and at least one pharmaceutical acceptable carrier.

According to one embodiment, treating a disease or disorder associated with binding of an agent to the GABA receptor comprises reversing the effect caused by the binding of the agent to the GABA receptor.

According to another embodiment, the agent is a benzodiazepine a non-benzodiazepine the binding of which to the GABA receptor causes sedation.

According to yet another aspect, the present invention provides a method for treating a disease or disorder comprising administering to a patient in need thereof a pharmaceutical composition comprising as an active ingredient a flumazenil complex, and at least one pharmaceutical acceptable carrier, wherein the disease or disorder is selected from the group consisting of: excessive sleepiness, alcohol intoxication and hepatic encephalopathy.

According to yet another aspect, the present invention provides a method for treating excessive sleepiness comprising administering to a patient in need thereof a pharmaceutical composition comprising as an active ingredient a flumazenil complex, and at least one pharmaceutical acceptable carrier.

According to one embodiment, the excessive sleepiness is selected from the group consisting of: excessive sleepiness associated with hypersomnia, excessive sleepiness associated with drowsiness, symptoms associated with overdose of a sleep drug, excessive sleepiness associated with sedation and anesthesia induced by a sleep drug, excessive sleepiness associated with sleep drug addiction, excessive sleepiness associated with stimulant addiction, Alzheimer's disease, anxiety, schizophrenia, specifically, schizophrenia associated with excessive sleepiness, the rebound effect of a sleep drug, balance impairment induced by a sleep drug or any combination thereof.

According to another embodiment, the excessive sleepiness is caused by alcohol intoxication.

According to yet another embodiment, the stimulant is methamphetamine. According to yet another embodiment, treating excessive sleepiness associated with stimulant addiction further comprises administering the flumazenil complex, or the pharmaceutical composition comprising same, in combination with hydroxyzine and gabapentin.

According to yet another embodiment, the sleep-drug is selected from the group consisting of a benzodiazepine, a benzodiazepine modulator, a benzodiazepine analog, a non-benzodiazepine, a 5-HT2A receptor antagonist, a melatonin receptor agonist, an orexin receptor antagonist, a selective serotonin reuptake inhibitor (SSRI), an antihistamine and an herbal product.

According to yet another embodiment, the sleep drug is a sedative/hypnotic drug.

According to yet another embodiment, the sleep drug is a benzodiazepine sedative/hypnotic drug. According to yet another embodiment, the benzodiazepine sleep drug is selected from the group consisting of alprazolam, bromazepam, clonazepam, clotiazepam, cloxazolam, diazepam, estazolam, etizolam, fludiazepam, flunitrazepam, flurazepam, halazepam, haloxazolam, lorazepam, medazepam, midazolam, nimetazepam, nitrazepam, olanzapine, oxazepam, quazepam, temazepam and triazolam.

According to yet another embodiment, treating excessive sleepiness comprises reversing benzodiazepine-induced sedation and anesthesia following therapeutic or diagnostic procedures.

According to yet another embodiment, the sleep-drug is a non-benzodiazepine sedative/hypnotic drug. According to yet another embodiment, the non-benzodiazepine sleep drug is selected from the group consisting of adipiplon (NG-2-73), agomelatine, almoxerant (ACT-078573), brotizolam, diphenhydramine, divaplon, doxepin, eplivanserin (SR 46349), doxylamine succinate, eszopiclone, indiplon, ocinaplon, pagoclone, pazinaclone, pruvanserin (EMD 281014), suproclone, suriclone, L-tryptophan, 5-hydroxy-L-tryptophan, melatonin, melatonin receptor agonists, such as VEC-162 and PD-6735, muramyl dipeptide, ramelteon, sleep-promoting substance, uridine, volinanserin (M-100907), zaleplon, zolpidem, imidazopyridine hypnotic zolpidem, APD125, ACP-103, PD 200-390, HY10275, GW649863 and EVT-201.

According to yet another aspect, the present invention provides a method for treating alcohol intoxication comprising administering to a patient in need thereof a pharmaceutical composition comprising the flumazenil complex of the invention, and at least one pharmaceutical acceptable carrier.

According to one another embodiment, the excessive sleepiness caused by alcohol intoxication is treated by any one or more of reversing the effects of alcohol intoxication, reducing the effects of alcohol intoxication, alleviating the effects of alcohol intoxication and/or improving performance after alcohol consumption.

According to yet another aspect, the present invention provides a method for treating hepatic encephalopathy, comprising administering to a subject in need thereof the flumazenil complex of the invention or a pharmaceutical composition comprising same.

According to another embodiment, the route of administration is selected from the group consisting of: oral, buccal, sublingual, transdermal, transmucosal, intranasal, intravenous (i.v.), intraperitoneal (i.p.), intramuscular (i.m.), subcutaneous (s.c.) or intra-thecal (i.t.). Each possibility represents a separate embodiment of the present invention.

According to yet another embodiment, the methods of the invention further comprise co-administering, concomitantly or in sequence, a pharmaceutical composition comprising a flumazenil complex together with a wakefulness promoting agent. According to yet another embodiment, the wakefulness promoting agent is selected from the group consisting of modafinil, armodafinil, adrafinil, methylphenidate, nefazodone, sodium oxybate, phentermine, pemoline, adrenaline, methylxantines, theobromine, caffeine and a combination thereof.

According to yet another aspect, the present invention provides a flumazenil complex for the treatment of excessive sleepiness or hepatic encephalopathy, the flumazenil complex comprises flumazenil and a complexation agent, with the proviso that the complexation agent is other than cyclodextrin or meglumine.

According to yet another aspect, the present invention provides a flumazenil complex for the treatment of excessive sleepiness or hepatic encephalopathy, the flumazenil complex comprises flumazenil and an aromatic complexation agent, such as, nicotinamide derivatives.

According to yet another aspect, the present invention provides a pharmaceutical composition comprising a flumazenil complex as the active ingredient, for the treatment of excessive sleepiness or hepatic encephalopathy.

Other objects, features and advantages of the present invention will become clear from the following description.

DETAILED DESCRIPTION OF THE INVENTION

Figure 1:
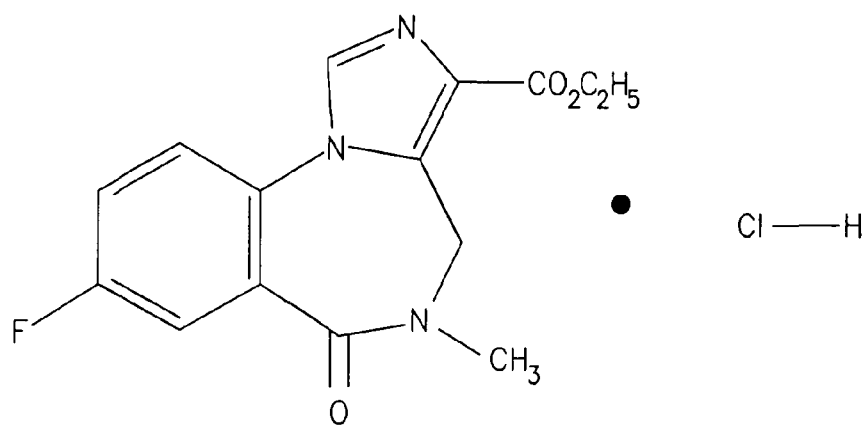
FIG. 1 is a schematic presentation of a flumazenil hydrochloric acid salt.

The present invention is directed to pharmaceutically acceptable flumazenil salts comprising flumazenil and a counter-ion. In addition, the present invention provides pharmaceutically acceptable flumazenil complexes comprising flumazenil with a stacking complexation agent, such as an aromatic complexation agent, wherein the complexation agent is other than meglumine and cyclodextrin.

As used herein, "pharmaceutically acceptable salts" refer to derivatives of the disclosed compounds wherein the parent compound is modified by making acid or base salts thereof. Examples of pharmaceutically acceptable salts include, but are not limited to, inorganic or organic acid salts of basic residues such as amines and the like. The pharmaceutically acceptable salts include conventional non-toxic salts of the parent compound formed, for example, from inorganic or organic acids, such as mineral acids (e.g., HCl) and nicotinic acids. Conventional non-toxic salts include those derived from inorganic acids, such as, hydrochloric, hydrobromic, sulfuric, sulfamic, phosphoric, nitric and the like; and the salts prepared from organic acids, such as, acetic, propionic, succinic, glycolic, stearic, lactic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

According to particular embodiments, the salts of the present invention are acid addition salts of flumazenil. According to some embodiments, the salts of the present invention are acid addition salts of flumazenil other than the acid addition salt flumazenil HCl.

Acid addition salts may, for example, be formed by mixing a solution of the compound of the present invention with a solution of a pharmaceutically acceptable acid, such as, hydrochloric acid, sulfuric acid, acetic acid, trifluoroacetic acid and benzoic acid.

The terms "acid salt" and "acid addition salts" are synonymous and refer to a class of salts formed by the partial neutralization of protic, diprotic or polyprotic acids. In diprotic or polyprotic acids, because the parent acid is only partially neutralized, one or more replaceable protons remain. Acid salt compounds can act either as an acid or a base: addition of a suitably strong acid will restore protons, and addition of a suitably strong base will remove protons. The pH of a solution of an acid salt will depend on the relevant equilibrium constants and the amounts of any additional base or acid.

According to some embodiments, the flumazenil complex of the invention comprises flumazenil and a complexation agent, wherein the complexation agent is preferably a hydrotope, other than cyclodextrins or meglumine, preferably, an aromatic stacking complexation agent.

The term "hydrotopes" as used herein, refers to compounds which are capable of opening up the water structure associated with hydrophobic (lipophilic) and other molecules. These compounds may be used to enhance the aqueous solubility of poorly water-soluble substances. Non limiting examples of hydrotopes includes sodium benzoate, sodium hydroxybenzoate, sodium salicylate, nicotinamide, sodium nicotinate, urea, sodium gentisate, gentisic acid ethanolamine, sodium toluate, sodium aminobenzoates, sodium anthranilate, sodium butylmonoglycolsulfate, resorcinol and the like. Each possibility represents a separate embodiment of the present invention.

As used herein, the term "stacking complexation agent" refers to complexation agent that forms a layered structure consisting of planar layers of the complexation agent stacked above and below the compounds with which the complex is formed. This mechanism is particularly suitable for complexing insoluble molecules having a relatively planar configuration, such as flumazenil. Preferably, the stacking complexation agent also has a relatively planar configuration. Preferred stacking complexation agents include nicotinamide and nicotinamide derivatives.

The term "nicotinamide derivatives" as used herein is meant to include any derivative of nicotinamide capable of forming a complex with flumazenil with improved solubility compared to the solubility of uncomplexed flumazenil. Acceptable nicotinamide derivatives include, but are not limited to, the nicotinamide derivatives disclosed in any one or more of: U.S. Pat. Nos. 7,056,934 and 7,153,870; WO 2008/071665; Kuramochia et al., Bioorganic & Medicinal Chemistry, Vol. 13(12), 2005, 4022-4036; and Fonti et al., Nucl Med. Biol., 1999, 26(6):681-6, among others. Further non-limiting examples of nicotinamide derivatives include 2-amino-nicotinamide derivatives, 5-phenyl-nicotinamide derivatives, and 6-substituted nicotinamide derivatives.

Complex formation, which is non-covalent in nature, may be achieved by mixing appropriate ratios of the solvent-derived composition and the hydrotope or mixtures thereof in a suitable liquid vehicle, which may be aqueous, organic or a combination of both. Additional excipients, such as, surfactants, polyols, disaccharides may be added to facilitate complexation or for assisting in dispersability. The resultant complex may be isolated as a dry powder by any process known in the art (co-precipitation and drying, evaporation of the liquid vehicle, spray drying, lyophilization etc.). Particle size may be reduced by any standard technique known in the art, if desired. The resultant hydrotope complex may be used without further modification or may be compounded into a variety of other formulations or vehicles as required.

In a particular embodiment, the flumazenil stacking complex of the invention is a flumazenil nicotinamide complex. Nicotinamide, also known as niacinamide and nicotinic acid amide, is the amide of nicotinic acid (vitamin B3/niacin) and is also known as 3-pyridinecarboxamide, nicotinic acid amide and Vitamin PP.

Nicotinamide has over the past years been given at high doses for a variety of therapeutic applications. For regulatory purposes nicotinamide is classed as a food additive rather than a drug, a category that does require the formal safety evaluation normally expected of new drugs and therapies. Overall, and as detailed hereinafter, nicotinamide is considered safe. The therapeutic index of nicotinamide is wide but at very high doses (i.e. in megadoses) reversible hepatotoxicity has been reported in animals and humans. Minor abnormalities of liver enzymes can infrequently occur at the doses used for diabetes prevention. There is no evidence of teratogenicity from animal studies and there is no evidence of oncogenicity in human. Growth inhibition was shown in rats but growth in children is unaffected. In addition, minor degrees of insulin resistance attributed to nicotinamide have been reported. High-dose nicotinamide, i.e. in excess of 3 gm/day, should be considered as a drug with toxic potential at adult doses and unsupervised use should be discouraged.

The ratio of flumazenil:nicotinamide in the stacking complex of the invention is within the range of 1:1 to 1:2. In certain embodiments the flumazenil:nicotinamide ratio in the complex of the invention is about 1:1.5. This ratio increases the solubility of flumazenil such that formulations comprising about 1% flumazenil with excellent solubility are obtained. The amount of nicotinamide in such formulations is about 1.5%. Accordingly, for example, a pharmaceutical composition comprising 3 mg of flumazenil, which is about the maximal daily dose allowed for flumazenil, corresponds to 4.5 mg of nicotinamide. An amount of 4.5 mg nicotinamide is lower by a factor of about 670 from 3 gr. (where 3 gr. is considered high dose and potentially toxic, for nicotinamide).

The marginal toxicity of nicotinamide renders it advantageous over other complexation agents. For example, cyclodextrins, another family of complexation agents, which increase the solubility of poorly soluble compounds by means of inclusion, are found toxic at relatively low concentrations, although there are significant differences between the cytotoxicity of the various cyclodextrin derivatives.

For example, the quantity of solubilized paclitaxel (as Taxol®), a poorly soluble drug, increased with cyclodextrin concentration. However, some of the cyclodextrins tested in this study were found toxic in mice with a maximum tolerated dose of 2 g/kg body weight, which is the quantity of cyclodextrin required to administer paclitaxel at 10 mg/kg. Other cyclodextrins allowed paclitaxel administration at higher doses yet had a maximum tolerated dose of 25 mg drug/kg.

Another advantage attributed to the flumazenil-nicotinamide complex of the invention is long shelf life. As exemplified hereinbelow, the flumazenil complex of the invention has an exceptional stability, during days, weeks and month of storage at room temperature and even at higher temperatures.

Without being bound to any theory or mechanism it is worth noting that cyclodextrins and nicotinamide increase solubility by different complexation mechanisms. It has been suggested that nicotinamide complex with hydrophobic ('guest') species is made out of a stack of nicotinamide and the guest species, whereby one or more 'sheets' of nicotinamide are stacked above and below a layer of the hydrophobic species. Clearly, stack formation depends on the 3D configuration of the members of the complex. While nicotinamide is substantially planar, for the formation of a stacked complex, it is generally required that the hydrophobic guest species would also be planar. Complex formation by cyclodextrins is exerted by way of inclusion. Cyclodextrins form a cavity, having an inner hydrophobic core and an outer hydrophilic core, where the cavity traps the hydrophobic species. The resulting complex exhibits modified physical and chemical properties, mostly in terms of water solubility. Cyclodextrins are relatively large molecules (molecular weight ranging from almost 1000 to over 1500), with a hydrated outer surface, and under normal conditions, cyclodextrin molecules will only permeate biological membranes with considerable difficulty.

The present invention further provides a pharmaceutical composition comprising the flumazenil salt or complex as the pharmaceutically active ingredient and a pharmaceutical acceptable carrier.

The pharmaceutical compositions according to the present invention preferably comprise one or more pharmaceutical acceptable carriers and the active constituent(s). The term "carrier" refers to a diluent, adjuvant, excipient, or vehicle with which the therapeutic is administered. The carriers in the pharmaceutical composition may comprise a binder, such as microcrystalline cellulose, polyvinylpyrrolidone (polyvidone or povidone), gum tragacanth, gelatine, starch, lactose or lactose monohydrate; a disintegrating agent, such as alginic acid, maize starch and the like; a lubricant or surfactant, such as magnesium stearate, or sodium lauryl sulphate; a glidant, such as colloidal silicon dioxide; a sweetening agent, such as sucrose or saccharin; and/or a flavoring agent, such as peppermint, methyl salicylate, or orange flavoring. More examples of the carriers include, but not limited to, physiological saline, polyethylene glycol, ethanol, vegetable oils, isopropyl myristate, etc. For topical administration, the compounds of the present invention can be formulated in the form of ointment or cream. Each possibility represents a separate embodiment of the present invention.

The carrier(s) must be "acceptable" in the sense of being compatible with the other ingredients of the composition and not deleterious to the recipients thereof.

The pharmaceutical composition comprising the flumazenil salt or complex of the invention as the active ingredient, may further comprise cyclodextrins, at least one solubilizing agent, at least one penetration enhancer, and at least one preservative. The pharmaceutical composition may further comprise additional excipients, such as, flavoring agents, among others.

The solubilizing agent is preferably a polar solvent such as mono- or poly-alcohols of linear or branched configuration (e.g., C1 to C8 alcohols). Non-limiting examples include methanol, ethanol, propanol, iso-propanol, n-butanol, sec-butanol, isobutanol, t-butanol, n-pentanol, 2-pentanol, 3-pentanol, neopentanol, 1-hexanol, 2-hexanol, 3-hexanol, 1-heptanol, 2-heptanol, 1-octanol, as well as any geometrical isomers, enantiomers and diastereomers of any of the foregoing. Other suitable polar solvents include glycols such as ethylene glycol, propylene glycol and their polymers having a molecular weight between 400 and 1000. Each possibility represents a separate embodiment of the present invention. In one particular embodiment, the solubilizing agent is a combination of ethanol and propylene glycol.

Preferred solubilizing agents include alcohols, glycols and combinations thereof. Each possibility represents a separate embodiment of the present invention.

According to some embodiments, the solubilizing agent in the composition of the invention comprises a combination of an alcohol and a glycol wherein the alcohol:glycol ratio is at least 1.5:1 or in the range of 1.5:1 to 5:1. The solubilizing agent, preferably in the form of combination of an alcohol and a glycol, may be at least 40%, or in the range of 40% to 60%., of the total weight of the pharmaceutical composition of the invention.

The expression "cyclodextrin" as used herein means α-, β- or γ-cyclodextrin or a derivative thereof. Suitable cyclodextrin derivatives for use in the formulations of the present invention include, but are not limited to the cyclodextrin listed above, e.g. hydroxypropyl derivatives of α-, β- and γ-cyclodextrin, sulfoalkylether cyclodextrins such as sulfobutylether β-cyclodextrin, alkylated cyclodextrins such as the randomly methylated β-cyclodextrin, and various branched cyclodextrins such as glucosyl- and maltosyl β-cyclodextrin. Other cyclodextrins are described in US patent publication US 2004/0186075, the contents of which are incorporated by reference in their entirety.

In one currently preferred embodiment, the cyclodextrin is hydroxypropyl β-cyclodextrin (HPCD). The cyclodextrin is preferably formulated in a buffer having a pH from about 3 to about 6. In one particular embodiment, the cyclodextrin (e.g., HPCD) is formulated in a citric acid buffer having a pH of about 4.

The cyclodextrin component of the formulations of the present invention may be present in an amount from about 10% to about 95% w/w, for example from about 30% to about 80%, from about 30% to about 75%, or about 60% based on the formulations of the invention. It is generally recognized that cyclodextrins act as true carriers by keeping the hydrophobic drug molecules in solution and delivering them to the surface of the biological membrane, e.g. skin, mucosa or the eye cornea, where they partition into the membrane. The relatively lipophilic membrane has low affinity for the hydrophilic cyclodextrin molecules and therefore they remain in the aqueous membrane exterior, e.g. the aqueous vehicle system, salvia or the tear fluid. Conventional penetration enhancers, such as alcohols and fatty acids, disrupt the lipid layers of the biological barrier. Cyclodextrins, on the other hand, may act as penetration enhancers by increasing drug availability at the surface of the biological barrier.

Therapeutic formulations suitable for oral administration, e.g. tablets and pills, may be obtained by compression or moulding, optionally with one or more accessory ingredients. Compressed tablets may be prepared by mixing the constituent(s), and compressing this mixture in a suitable apparatus into tablets having a suitable size. Prior to the mixing, the phanquinone may be mixed with a binder, a lubricant, an inert diluent and/or a disintegrating agent and the further optionally present constituents may be mixed with a diluent, a lubricant and/or a surfactant. A tablet may be coated or uncoated. An uncoated tablet may be scored. A coated tablet may be coated with sugar, shellac, film or other enteric coating agents. Each possibility represents a separate embodiment of the present invention.

Therapeutic formulations suitable for parenteral administration include sterile solutions or suspensions of the active constituents. An aqueous or oily carrier may be used. Such pharmaceutical carriers can be sterile liquids, such as water and oils, including those of petroleum, animal, vegetable or synthetic origin, such as peanut oil, soy bean oil, mineral oil, sesame oil and the like. Formulations for parenteral administration also include a lyophilized powder comprising flumazenil and, optionally, further active constituents, that is to be reconstituted by dissolving in a pharmaceutically acceptable carrier that dissolves the active constituents, e.g. an aqueous solution of carboxymethylcellulose and lauryl sulphate. Each possibility represents a separate embodiment of the present invention.

When the pharmaceutical composition is a capsule, it may contain a liquid carrier, such as fatty oil, e.g. cacao butter.

Additional suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. These compositions can take the form of solutions, suspensions, emulsion, tablets, pills, capsules, powders, sustained-release formulations and the like. The composition can be formulated as a suppository, with traditional binders and carriers such as triglycerides. Each possibility represents a separate embodiment of the present invention.

The formulations of the present invention may further comprise penetration enhancers, such as menthol. Other penetration enhancers that may be used in the formulations of the present invention include, but are not limited to, anionic surfactants (e.g. sodium lauryl sulphate, sodium dodecyl sulphate), cationic surfactants (e.g. palmitoyl DL camitine chloride, cetylpyridinium chloride), nonionic surfactants (e.g. polysorbate 80, polyoxyethylene 9-lauryl ether, glyceryl monolaurate, polyoxyalkylenes, polyoxyethylene 20 cetyl ether), lipids (e.g. oleic acid), bile salts (e.g. sodium glycocholate, sodium taurocholate), chitosan or a chitosan derivative, linalool, carvacrol, thymol, citral or t-anethole, and related compounds. Each possibility represents a separate embodiment of the present invention.

The formulations of the invention optionally further comprise at least one preservative. Any suitable preservative may be present in the formulation in the present invention. The preservative may be any pharmaceutically acceptable preservative, for example methyl 4-hydroxybenzoate (methyl paraben), ethyl 4-hydroxybenzoate (ethyl paraben), propyl 4-hydroxybenzoate (propylparaben), benzyl alcohol, sorbic acid, sodium benzoate, benzoic acid, and any combination thereof. Each possibility represents a separate embodiment of the present invention.

The formulation of the invention optionally further comprises a flavoring agent in an amount between 0.05 and 10 percent by weight of the total composition. In one embodiment, the flavoring agent is present in an amount between 0.1 and 2.5 percent by weight of the total composition. The flavoring agent is preferably selected from the group consisting of synthetic or natural oil of peppermint, oil of spearmint, citrus oil, fruit flavors, sweeteners (sugars, aspartame, saccharin, Estevia, etc.), and mixtures thereof. Menthol can also act as a flavoring agent.

In yet another embodiment, the therapeutic compound can be delivered in a controlled release system. The term "controlled release" is used herein to refer to a pharmaceutical dosage form in which release of the active ingredient is timed or modified to a rate sufficient to maintain the desired therapeutic level over an extended period of time. The release may be a "sustained release" or a "delayed release" such that release of the active ingredient from the pharmaceutical dosage form is other than promptly after administration of the dosage form, but rather is withheld or delayed following administration.

In one embodiment, a pump may be used. In another embodiment, polymeric materials can be used. In yet another embodiment, a controlled release system can be placed in proximity of the therapeutic target, i.e., the central nervous system, thus requiring only a fraction of the systemic dose. Other controlled release systems are discussed, for example, in U.S. Pat. No. 5,120,548 which is directed a controlled-release drug delivery device comprised of swellable polymers. U.S. Pat. No. 5,073,543 also describes controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. Biodegradable microparticles are also known for use in controlled-release formulations. U.S. Pat. No. 5,733,566 describes the use of polymeric microparticles that release antiparasitic compositions.

The controlled-release of the active ingredient may be stimulated by various inducers, for example, pH, temperature, enzymes, water, or other physiological conditions or compounds.

The terms "composition," "formulation" and "dosage form" are used herein interchangeably to encompass formulated preparations comprising one or more pharmacologically active drugs, and one or more pharmaceutically acceptable excipients, diluents or carriers. Compositions, formulations and dosage forms can be designed for administration by all possible administration routes to achieve the desired therapeutic response. The terms used may refer to the physical format of the product which is dispensed and administered to the patient, for example, a capsule or a patch. Alternately or in addition, the terms used may refer to any of: the mode of administration, the mode of delivery or the mode of release of the drug, for example a transdermal delayed release formulation.

The compounds of the present invention may be formulated into injections by dissolving, suspending or emulsifying water-soluble solvent such as saline and 5% dextrose, or in water-insoluble solvents such as vegetable oils, synthetic fatty acid glyceride, higher fatty acid esters and propylene glycol. The formulations of the invention may include any of conventional additives such as dissolving agents, isotonic agents, suspending agents, emulsifiers, stabilizers and preservatives.

According to yet another aspect, the present invention provides a method for treating a disease or disorder associated with binding of an agent to the GABA receptor, comprising administering to a patient in need thereof a pharmaceutical composition comprising an active ingredient selected from flumazenil salt and flumazenil complex, and at least one pharmaceutical acceptable carrier. Thus, the pharmaceutical composition of the invention is intended for use as an antidote for GABA related sedatives/hypnotics.

Preferably, the disease or disorder is excessive sleepiness, the agent is a benzodiazepine or a non-benzodiazepine, and the effect is sedation.

As used herein, the term "treating" encompasses substantially ameliorating, relieving, alleviating and preventing symptoms of a disease, disorder or condition in a subject.

As used herein, the term "administering" refers to delivery of a pharmaceutical compound to a subject by any means that does not affect the ability of the compound to perform its intended function.

The terms "sleep drug" is used herein in reference to pharmaceutical agents used for inducing and/or maintaining sleep, in particular, prescription sleep drugs that are classified as hypnotics/sedatives. The sleep-drug may be a sedative/hypnotic drug, a benzodiazepine, a benzodiazepine modulator, a benzodiazepine analog, a non-benzodiazepine, a 5-HT2A receptor antagonist, a melatonin receptor agonist, an orexin receptor antagonist, a selective serotonin reuptake inhibitor (SSRI), an antihistamine and an herbal product.

Suitable benzodiazepine sleep drugs include alprazolam, bromazepam, clonazepam, clotiazepam, cloxazolam, diazepam, estazolam, etizolam, fludiazepam, flunitrazepam, flurazepam, halazepam, haloxazolam, lorazepam, medazepam, midazolam, nimetazepam, nitrazepam, olanzapine, oxazepam, quazepam, temazepam and triazolam.

Suitable non-benzodiazepine sleep drug include adipiplon, agomelatine, almoxerant, brotizolam, diphenhydramine, divaplon, doxepin, eplivanserin, doxylamine succinate, eszopiclone, indiplon, ocinaplon, pagoclone, pazinaclone, pruvanserin (EMD 281014), suproclone, suriclone, L-tryptophan, 5-hydroxy-L-tryptophan, melatonin, melatonin receptor agonists, muramyl dipeptide, ramelteon, uridine, volinanserin, zaleplon, zolpidem, imidazopyridine hypnotic zolpidem, APD125, ACP-103, PD 200-390, HY10275, GW649863 and EVT-201

As used herein, the term "effective amount" refers to an amount of a pharmaceutical compound sufficient to achieve its desired effect.

According to one embodiment, the excessive sleepiness is selected from the group consisting of: excessive sleepiness associated with hypersomnia, excessive sleepiness associated with drowsiness, symptoms associated with overdose of a sleep drug, excessive sleepiness associated with alcohol intoxication, excessive sleepiness associated with sedation and anesthesia induced by a sleep drug, excessive sleepiness associated with sleep drug addiction, excessive sleepiness associated with stimulant addiction, the rebound effect of a sleep drug, balance impairment induced by a sleep drug or any combination thereof.

According to certain embodiments, treating excessive sleepiness comprises reversing benzodiazepine-induced sedation and anesthesia following therapeutic or diagnostic procedures.

As used herein, the term "hypersomnia" refers to chronic or recurrent bouts of excessive sleepiness, characterized by one or more of near-daily diurnal sleep episodes, excessive naps, abnormally prolonged sleep intervals, a perception of non-restorative sleep, and difficulty in making the transition from sleep to wakefulness. Hypersomnia may be one or more of: shift work sleep disorder; narcolepsy; obstructive sleep apnea/hypopnea syndrome; REM behavior disorder; frontal nocturnal dystonia; restless legs syndrome; nocturnal movement disorder; Kleine-Levin syndrome; Parkinson's disease; Alzheimer's disease, schizophrenia, anxiety, schizophrenia (in particular, schizophrenia associated with excessive sleepiness), excessive sleepiness; hypersomnia; idiopathic hypersomnia; recurrent hypersomnia; endozepine related recurrent stupor; and amphetamine resistant hypersomnia.

According to yet another embodiment, the excessive sleepiness is caused by alcohol intoxication.

According to yet another aspect, the method of the invention is directed to treating alcohol intoxication.

The term "alcohol intoxication" means overdose of alcohol (e.g., ethanol) leading to behavioral impairment. A person is said to suffer from alcohol intoxication when the quantity of alcohol the person consumes exceeds the individual's tolerance for alcohol and produces behavioral or physical abnormalities. In other words, the person's mental and physical abilities are impaired.

In this respect is it noted that the term alcohol refers to the generic term for ethanol, which is a particular type of alcohol produced by the fermentation of many foodstuffs—most commonly barley, hops, and grapes. Other types of alcohol commonly available such as methanol (common in glass cleaners), isopropyl alcohol (rubbing alcohol), and ethylene glycol (automobile antifreeze solution) are highly poisonous when swallowed, even in small quantities. Ethanol produces intoxication because of its depressive effects on various areas of the brain causing these impairments in a progressive order as the person gets more and more drunk. Symptoms of alcohol intoxication and/or impaired performance after alcohol consumption include disinhibition of normal social functioning (e.g., excessive talking), loss of memory, confusion, disorientation, uncoordinated movement, progressive lethargy, coma, or ultimately death.

According to one another embodiment, treating excessive sleepiness caused by alcohol intoxication is selected from the group consisting of: reversing the effects of alcohol intoxication, reducing the effects of alcohol intoxication, alleviating the effects of alcohol intoxication and improving performance after alcohol consumption.

According to yet another aspect, the method of the invention is directed treating hepatic encephalopathy with the flumazenil formulation.

The method of the invention provides an improved treatment of hepatic encephalopathy. First, the pharmaceutical compositions of the present invention are suitable for oral, sublingual or transdermal administration. Second, the pharmaceutical composition of the present invention includes much higher concentrations of flumazenil, of about 0.4 to 2%. This concentration is higher by two orders of magnitude from the concentration of flumazenil in the commercially available flumazenil formulations that are known to date. Thereby the pharmaceutical compositions and methods of the present invention provide advantageous patient compliance. In addition, the present invention provides attractive routes for the delivery of flumazenil (e.g. sub-mucosaland and transdermal) thereby averting the need for admission to health centers.

Without being bound by any theory or mechanism, administering the salts and complexes of the present invention by submucosal or sublingual or transdermal routes, bypasses the first pass effect (through the liver). This mechanism probably confers a material advantage in the treatment of the aforementioned diseases and disorders (residual effect of hypnotics, sedation, hepatic encephalopathy, etc.). Hepatic encephalopathy refers to a complex neuropsychiatric syndrome, which may complicate acute or chronic hepatic failure. It is characterized by changes in mental state including a wide range of neuropsychiatric symptoms ranging from minor not readily discernible signs of altered brain function, overt psychiatric and/or neurological symptoms to deep coma. Accordingly, the methods to estimate treatment effects and treatment outcomes are highly variable. The majority of hepatic encephalopathy occurs in patients with cirrhosis, often associated with spontaneous or iatrogenic portal-systemic shunting. Hepatic encephalopathy is generally considered a reversible metabolic encephalopathy. Traditionally, hepatic encephalopathy has been considered to be secondary to the accumulation of toxic products, which have not been metabolized by the liver. Various hypotheses have been suggested, e.g., alterations in the permeability of the blood-brain barrier, abnormal neurotransmitter balance, altered cerebral metabolism, and increased amounts of endogenous benzodiazepine-like compounds—the gamma-amino butyric acid (GABA)/benzodiazepine hypothesis. GABA is the principal inhibitory neurotransmitter in mammals that acts by binding to a receptor on a 'supramolecular complex' called the GABA/benzodiazepine complex, which also has binding sites for benzodiazepines and barbiturates. By binding to the GABA/benzodiazepine complex, benzodiazepines cause sedation through neural inhibition. It has been suggested that liver failure leads to the accumulation of substances that bind to the GABA/benzodiazepine complex resulting in neural inhibition which may progress to coma. Accordingly, a benzodiazepine-receptor antagonist, flumazenil, has been assessed in the treatment of hepatic encephalopathy in the hope of reversing neuropsychiatric symptoms related to the accumulation of endogenous benzodiazepine.

As detailed above, Als-Nielsen et al. (ibid) disclose the use of flumazenil, administered via intravenous infusion of 1 mg flumazenil in 20 ml saline solution (0.005%) over 3-5 minutes, for treating hepatic encephalopathy. Als-Nielsen reports that flumazenil had a significant beneficial effect on short-term improvement of hepatic encephalopathy in patients with cirrhosis and a highly favorable prognosis but had no significant effect on recovery or survival.

The methods of the invention may be used in conjunction with insomnia treatment modalities, and serve to eliminate or diminish residual soporific effects associated with administration of sleep drugs. The invention is effective for counteracting excessive sleepiness induced by a wide variety of sleep drugs. Such sleep drugs include benzodiazepine and non-benzodiazepine drugs which are classified as hypnotics/sedatives, as well as other prescription and non-prescription sleep drugs, including those classified as 5-$HT_{2A}$ receptor antagonists, melatonin receptor agonists, orexin receptor antagonists, selective serotonin reuptake inhibitors (SSRIs), and other sleep inducing agents such as antihistamines, melatonin and certain herbal products. It is to be specifically understood that a particular sleep drug may be classified under more than one of the aforementioned categories.

According to another embodiment, the route of administration is selected from the group consisting of: oral, buccal, sublingual, transdermal, transmucosal, intranasal, intravenous (i.v.), intraperitoneal (i.p.), intramuscular (i.m.), subcutaneous (s.c.) or intra-thecal (i.t.).

For buccal administration, buccal tablets or sublingual tablets may be used. These tablets are typically small, flat and soft, designed to be placed in the side of the cheek (i.e. buccal cavity) or designed to be placed under the tongue, to be directly absorbed through the buccal mucosa for a systemic effect. Other dosage forms suitable for buccal administration are, for example, oral films administered on the gyngiva or tongue.

Sublingual spray is also a buccal formulation for delivery to the sublingual mucosa in the form of a spray for a systemic effect, typically provided in spray actuators, designed to access the mucosal surfaces under the tongue or the lips.

For transdermal delivery of the composition of the invention, the composition may be provided in the form of a patch. The major approaches for transdermal delivery include use of chemical penetration enhancers; physical enhancers, such as ultrasound, iontophoresis, electroporation, magnetophoresis, and microneedles; vesicles; particulate systems, such as those incorporating liposomes, niosomes, transfersomes, microemulsions, or solid lipid nanoparticles, as described for example in Rizwan et al., Recent Pat Drug Deliv Formul., 2009, 3(2):105-24.

Suitable penetration enhancers for transdermal delivery include, for example, saturated and unsaturated fatty acids and their esters, alcohols, monoglycerides, diethanolamines, N,N-dimethylamines such as linolenic acid, linolenyl alcohol, oleic acid, oleyl alcohol, stearic acid, stearyl alcohol, palmitic acid, palmityl alcohol, myristic acid, myristyl alcohol, 1-dodecanol, 2-dodecanol, lauric acid, decanol, capric acid, octanol, caprylic acid, 1-dodecylazacycloheptan-2-one, ethyl caprylate, isopropyl myristate, hexamethylene lauramide, hexamethylene palmitate, capryl alcohol, decyl methyl sulfoxide, dimethyl sulfoxide, salicylic acid and its derivatives, N,N-diethyl-m-toluamide, 1-substituted azacycloalkan-2-ones, propylene glycol, polyethylene and glycol monolaurate. Any compound compatible with flumazenil, and that has transdermal permeation enhancing activity may be selected.

Creams for transdermal delivery of flumazenil typically include gelling agents, for example, hydroxy methyl cellulose, hydroxypropyl cellulose, tragacanth, sodium alginate, gelatin, methylcellulose, sodium carboxymethylcellulose and polyvinyl alcohols.

The efficacy of the methods described herein may be assessed, for example by direct observation of behavioral and physiological properties, by self-reporting, and/or by various well-known electrophysiological methods and performance skill methods. Such methods include, for example, examining electroencephalograph (EEG) activity amplitude and frequency patterns, examining electromyogram activity, and examining the amount of time during a measurement time period, in which a mammal is awake or exhibits a behavioral or physiological property characteristic of wakefulness.

Objective and subjective tests for wakefulness, alertness and performance include, for example, the Epworth Sleepiness Scale (Johns M W (1991) Sleep 14 (6): 540-5) and the Stanford Sleepiness Scale (Hoddes et al (1972) Psychophysiology 9:150).

Additional methods used to monitor or assess alertness/drowsiness levels in a subject prior to and following use of the methods disclosed herein may employ various devices for measurement of eye position or closure, assumed to correlate with alertness/drowsiness, as disclosed for example in U.S. Pat. Nos. 5,689,241; 5,682,144 and 5,570,698.

The flumazenil compositions according to the present invention may also be used in conjunction with the administration of other pharmaceutically active compounds. In addition, the pharmaceutical composition according to the present invention may contain other pharmaceutically active compounds.

According to some embodiments, the methods of the invention further comprise co-administering, concomitantly or in sequence, the pharmaceutical composition comprising the flumazenil salt or flumazenil complex of the invention together with a wakefulness promoting agent. According to some embodiments, the wakefulness promoting agent is selected from the group consisting of modafinil, armodafinil, adrafinil, methylphenidate, nefazodone, sodium oxybate, phentermine, pemoline, adrenaline, methylxantines, theobromine, caffeine and a combination thereof.

The invention also provides a pharmaceutical pack or kit comprising one or more containers filled with one or more of the ingredients of the pharmaceutical compositions of the invention. Optionally associated with such container(s) can be a notice in the form described by a governmental agency regulating the manufacture, use or sale of pharmaceuticals or biological products, which notice reflects approval by the agency of manufacture, use or sale for human administration.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

Formulations of Flumazenil Salts and Complexes at 1% Flumazenil

Formulations with 1% flumazenil, in the form of a flumazenil salt or flumazenil complex, are presented in the following Tables. All formulations were evaluated for their appearance and only clear solutions, namely, clear solutions where a precipitate ('ppt') or slight precipitate ('sl-ppt') or a few particles ('part') are not formed, were tested for pH.

Compositions comprising nicotinamide as a complexation agent and meglumine resulted in clear solutions at first. Twelve hours later, in formulations containing the meglumine a precipitate was formed. Formulation No. 2 containing 4.5% nicotinamide showed less precipitate (designated 'ppt' in the Tables) after 12 hours compared to formulation No. 1 containing 1.5% nicotinamide (Table 1). This result indicates that high nicotinamide concentrations may be preferred, although not necessary in order to achieve the concept of the present invention. The appropriate pH values of a formulation intended for sublingual administration are between 4.0 to 9.0. The pH values of the nicotinamide-containing formulations meet this requirement (pH=5.0±0.2).

TABLE 1

Formulations of flumazenil-nicotinamide and flumazenil meglumine (% w/w)

| Material name | 1 | 2 | 3 | 4 | 5 | 6 |
|---|---|---|---|---|---|---|
| Flumazenil | 1 | 1 | 1 | 1 | 1 | 1 |
| Ethanol | 25 | 25 | 25 | | | |
| Propylene glycol | 25 | 25 | 25 | | | |
| Citric buffer 10 mM pH 4.0 | 47.4 | 44.4 | 48.7 | | | |
| Menthol in EtOH (1/1 w/w) | 0.1 | 0.1 | 0.1 | | | |
| Nicotinamide/WFI (1/2 w/w) | 1.5 | 4.5 | | | | |
| Benzalkonium chloride (BKC) 50% aq. solution | | | 0.2 | | | |
| Water (WFI) | | | | 98.67 | 98.67 | 98.356 |
| HCl | | | | 0.33 | | |
| $H_2SO_4$ | | | | | 0.33 | |
| Meglumine | | | | | | 0.644 |
| Appearance t = 0 | clear | clear | ppt | ppt | ppt | ppt |
| Appearance T = 12 h | sl-ppt | sl-ppt | | | | |
| pH | 5.06 | 5.15 | | | | |

TABLE 2

Formulations with cyclodextrin (HPCD; % w/w)

| Material name | 1' | 2' | 3' | 4' | 5' | 6' |
|---|---|---|---|---|---|---|
| Flumazenil | 1 | 1 | 1 | 1 | 1 | 1 |
| Ethanol | 20 | 20 | 20 | | | |
| Propylene glycol | 20 | 20 | 20 | | | |
| 30% HPCD in citric buffer | 57.4 | 54.4 | 58.7 | | | |
| 30% HPCD in water | | | | 98.67 | 98.67 | 98.36 |
| Menthol in EtOH (1/1 w/w) | 0.1 | 0.1 | 0.1 | | | |
| Nicotinamide/WFI (1/2 w/w) | 1.5 | 4.5 | | | | |
| BKC 50% aq. solution | | | 0.2 | | | |
| HCl | | | | 0.33 | | |
| $H_2SO_4$ | | | | | 0.33 | |
| Meglumine | | | | | | 0.644 |
| Appearance t = 0 | ppt | ppt | ppt | ppt | ppt | ppt |

TABLE 3

Formulations with flumazenil meglumine complex (% w/w)

| Material name | 7 | 8 | 9 | 8' | 9' |
|---|---|---|---|---|---|
| Flumazenil | 1 | 1 | 1 | 1 | 1 |
| Ethanol | 25 | 25 | 25 | 20 | 20 |
| Propylene glycol | 25 | 25 | 25 | 20 | 20 |
| WFI | 47.4 | 44.4 | | | |
| 30% HPCD in water | | | | 57.4 | 54.4 |
| Citrate buffer | | | 44.4 | | |
| Menthol in EtOH (1/1 w/w) | 0.1 | 0.1 | 0.1 | 0.1 | 0.1 |
| Meglumine in WFI (1/2 w/w) | 1.5 | 4.5 | 4.5 | 1.5 | 4.5 |
| Appearance t = 0 | clear | clear | clear | ppt | ppt |
| Appearance t = 12 h | sl-ppt | sl-ppt | ppt | | |
| pH | 10.91 | 11.32 | 10.50 | | |

TABLE 4

Formulations with flumazenil nicotinamide complex
and flumazenil meglumine complex (% w/w)

| Material name | 10 | 11 | 12 | 13 | 14 | 15 | 16 |
|---|---|---|---|---|---|---|---|
| Flumazenil | 1 | 1 | 1 | 1 | 1 | 1 | 1 |
| Ethanol | 25 | 25 | 25 | 30 | 35 | 35 | 40 |
| Propylene glycol | 25 | 25 | 25 | 20 | 20 | 15 | 10 |
| Citric buffer 10 mM pH 4.0 | 41.5 | 46.9 | 43.9 | 44.5 | 39.5 | 44.5 | 44.5 |
| Nicotinamide/WFI (1/2 w/w) | 7.5 | 1.5 | 4.5 | 4.5 | 4.5 | 4.5 | 4.5 |
| Meglumine in WFI (1/2 w/w) | | 0.6 | 0.6 | | | | |
| Appearance t = 0 | clear | clear | clear | clear | clear | clear | clear |
| pH, T-0 | 5.10 | 9.02 | 9.12 | 5.09 | 5.25 | 5.16 | 5.17 |
| Appearance t = 24-72 h | sl-ppt | ppt | ppt | sl-ppt | clear | clear | clear |
| Appearance t = 24-72 h | | 10.91 | 11.32 | 10.50 | | | |

Example 2

Formulations of Flumazenil (1.2 and 1.5% w/w) Nicotinamide Complex

Formulations containing 1.2 to 1.5% w/w flumazenil in the form of a flumazenil complex with nicotinamide were prepared and are presented in the following Table.

TABLE 5

Flumazenil formulations with flumazenil nicotinamide complex (% w/w)

| Material name | 14A | 15A | 16A | 14B | 16B | 17 | 18 | 19 | 20 |
|---|---|---|---|---|---|---|---|---|---|
| Flumazenil | 1.5 | 1.5 | 1.5 | 1.2 | 1.2 | 1.5 | 1.5 | 1.5 | 1.5 |
| Ethanol | 35 | 35 | 40 | 35 | 40 | 40 | 35 | 40 | 30 |
| Propylene glycol | 20 | 15 | 10 | 20 | 10 | 20 | 20 | 10 | 30 |
| Citric buffer 10 mM pH 4.0 | 39 | 44 | 44 | 39.3 | 44.3 | 34 | 36 | 41 | 34 |
| Nicotinamide/WFI (1/2 w/w) | 4.5 | 4.5 | 4.5 | 4.5 | 4.5 | 4.5 | 7.5 | 7.5 | 4.5 |
| Appearance T-0 | clear | clear | clear | clear | clear | clear | clear | clear | clear |
| pH, T-0 | 5.27 | 5.18 | 5.24 | 5.25 | 5.26 | 5.44 | 5.28 | 5.26 | 5.30 |
| Appearance T-24-72 h | sl-ppt | ppt | sl-ppt | clear | clear | clear | ppt | ppt | ppt |
| Appearance T-1 week | | | | part | clear | part | | | |

Example 3

Formulations of Flumazenil Nicotinamide Complexes and Menthol

Formulations containing 1.2% w/w flumazenil based on formulation 16 B (Table 6, above), were prepared with menthol and are presented in the following Table.

TABLE 6

Flumazenil formulations with 1.2 flumazenil (% w/w) and menthol

| | 0.2% menthol | | 0.1% menthol | |
|---|---|---|---|---|
| Material name | % | g | % | g |
| Flumazenil | 1.2 | 0.06 | 1.2 | 0.06 |
| Ethanol | 40 | 2 | 40 | 2 |
| Propylene glycol | 10 | 0.5 | 10 | 0.5 |
| Citric buffer 10 mM pH 4.0 | 43.9 | 2.195 | 44.1 | 2.205 |
| Nicotinamide/WFI (1/2 w/w) | 4.5 | 0.225 | 4.5 | 0.225 |

TABLE 6-continued

Flumazenil formulations with 1.2 flumazenil (% w/w) and menthol

| | 0.2% menthol | | 0.1% menthol | |
|---|---|---|---|---|
| Material name | % | g | % | g |
| Menthol/EtOH (1/1 w/w) | 0.4 | 0.02 | 0.2 | 0.01 |
| Appearance T-0 | clear | | clear | |
| pH, T-0 | 5.17 | | 5.25 | |
| Appearance T-24 h | part | | clear | |

The results are similar to the results obtained in the absence of menthol (see Tables 4-5, above) indicating that menthol is not necessary in order to achieve the concept of the present invention, particularly, the improved solubility of the flumazenil salts or complexes.

Example 4

HPLC Analysis of Flumazenil in the Presence of Nicotinamide

The conditions for determining by HPLC the presence of flumazenil in solutions containing flumazenil complex (1% (10 mg/g) or 1.2% (12 mg/g) flumazenil and 1.5% nicotinamide), were determined.

The details of the tested compounds were as follows:
Flumazenil [$C_{15}H_{14}FN_3O_3$], 303.29 g/mol (Chemagis, purity: 99.3%,)
Niacinamide USP (Nicotinamide) [$C_6H_6N_2O$], 122.12 g/mol
(Spectrum, purity: 99.5%)
The HPLC (High-performance liquid chromatography) agents were HPLC grade water, methanol, acetonitrile, ammonium acetate, ammonium acetate and acetic acid glacial. Analysis was performed utilizing the column Inertsil, G.L. Sciences, ODS-3V, 5 mm, 250×4.6 mm, C.N. 5020-01802 and the pre-column: Phenomex C18, 5 mm.
For Mobile Phase A, 13 mM Ammonium acetate buffer in water (pH adjusted at 4.40 with acetic acid) was utilized and acetonitrile for Mobile Phase B. Analysis was performed at column temperature of 30°±5° C., autosampler temperature of 10°±5° C., injection volume of 20 ml, PDA programmed 210 to 330 nm, sampling rate=2, resolution=1.2 and monitoring wavelength: 247 nm. The resulting gradient Table is given below.

TABLE 7

| Time (min) | Flow (ml/min) | % A | % B | Curve |
|---|---|---|---|---|
| 0 | 1 | 80 | 20 | 6 |
| 0.5 | 1 | 80 | 20 | 6 |
| 8.0 | 1 | 50 | 50 | 6 |
| 8.01 | 1.2 | 50 | 50 | 6 |
| 13.0 | 1.2 | 50 | 50 | 6 |
| 13.01 | 1.2 | 80 | 20 | 6 |
| 19.0 | 1 | 80 | 20 | 6 |

Samples of the following liquid formulations were prepared: Formulation 16 (Table 4; 1% flumazenil), Formulation 16B (Table 5; 1.2% flumazenil) and Formulation 16B with menthol (Table 6; 1.2% flumazenil). Solutions of flumazenil and of nicotinamide were made by mixing the dry compounds with the diluent (acetonitrile/water/acetic acid, 20/80/0.1 v/v/v).

Figure 2:
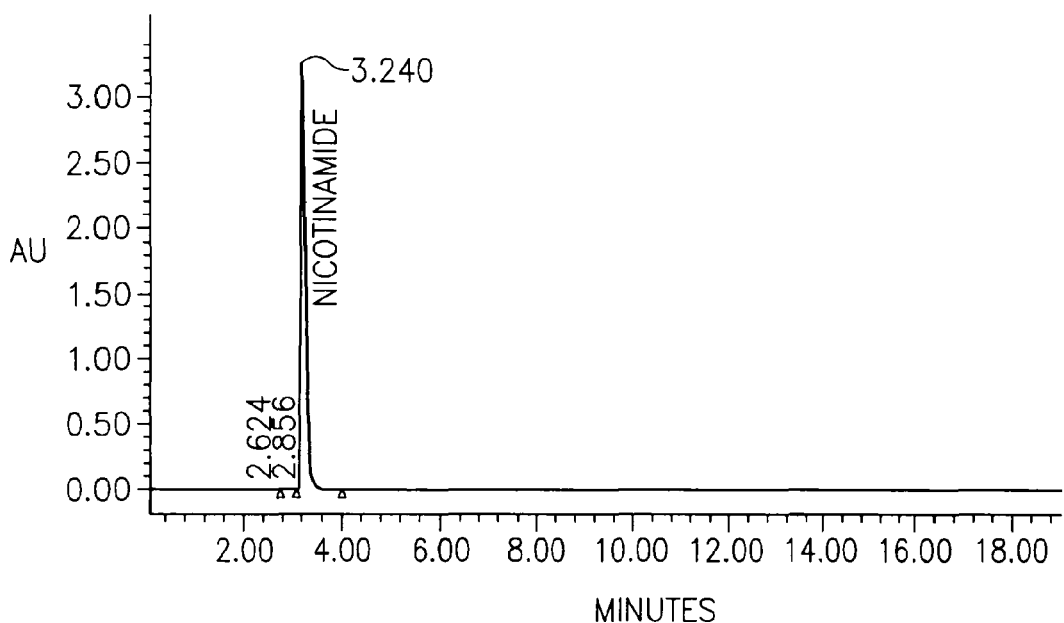
FIG. 2 exhibits a chromatogram of 0.6 mg/ml nicotinamide solution in diluents.
Figure 3:
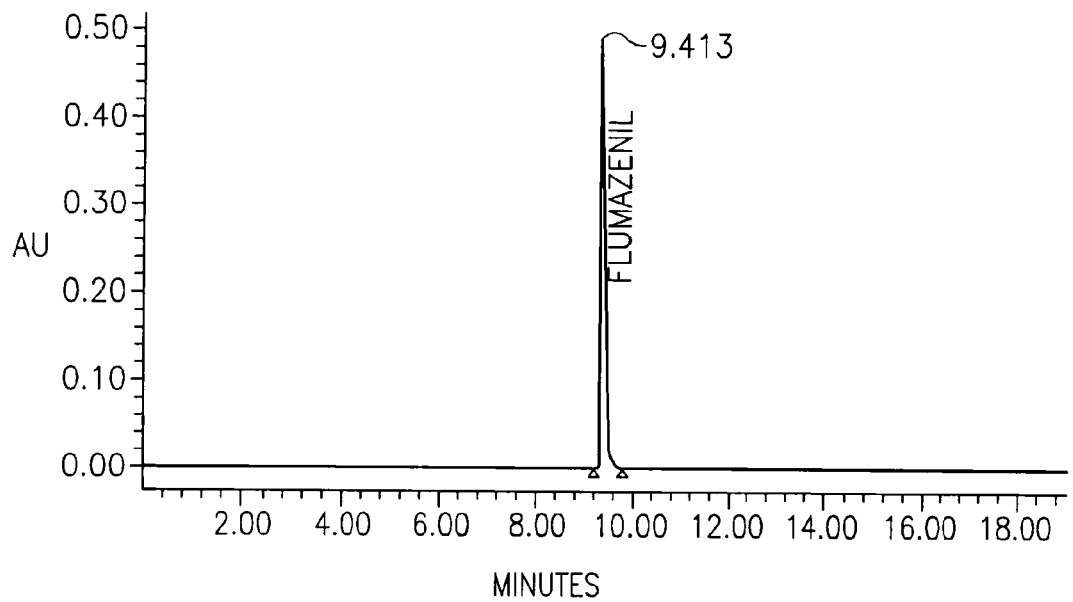
FIG. 3 shows a chromatogram of 40 µg/ml flumazenil solution in diluents.
Figure 4:
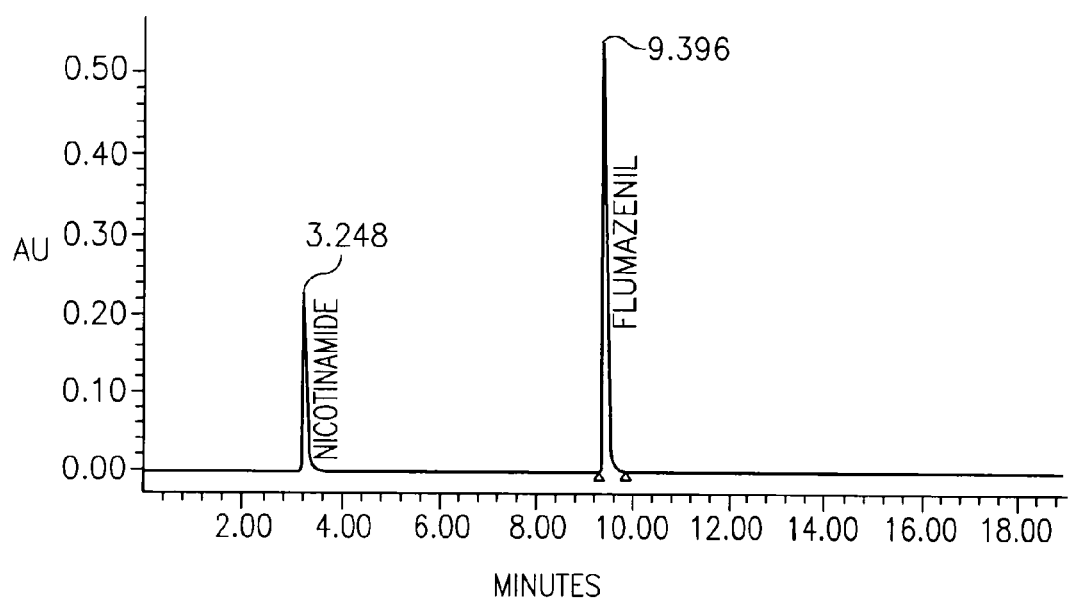
FIG. 4 shows a chromatogram of a flumazenil nicotinamide complex in diluents.

Nicotinamide solution was injected and nicotinamide was eluted at retention time (RT) of 3.2 min. Good resolution was obtained between nicotinamide and flumazenil, since the retention time of flumazenil is about 9.4 min. Representative chromatograms are presented in FIGS. 2-4.

Assay of flumazenil solutions was determined using single point calibration. Flumazenil standard solution 40 ug/ml was injected five times. Flumazenil sample solutions were prepared in triplicate and injected once. The assay (%) of flumazenil in a sample was calculated according to the following formula:

$$\text{Assay (\%)} = (W_{std} \times P \times D_{smp} \times A_{smp} / (D_{std} \times A_{std} \times \text{Dose} \times W_{smp})) \times 100$$

Where:
i. Wstd is the weight of flumazenil standard in mg;
ii. P is the purity of flumazenil standard (99.3%);
iii. Dstd is the dilution factor of the calibration solution (500);
iv. Dsmp is the dilution of the sample solution in ml (100 ml);
Wsmp is the weight of sample solution in the sample in mg;
v. Dose is the theoretical amount (%) of flumazenil in the solution;
vi. Astd is an average peak area of flumazenil for the five first injections of flumazenil calibration solution;
vii. Asmp is an average peak area of Flumazenil in the sample.

The assay results are summarized in the Table below.

TABLE 8

Flumazenil formulation analysis

| Formulation No. | Sample weight (mg) | Peak area | Assay (%) | Mean assay (%) |
|---|---|---|---|---|
| 16 | 412.18 | 2956920 | 103.64 | 103.8 |
| | 411.98 | 2964443 | 103.96 | |
| 16B | 338.43 | 2744305 | 97.63 | 100.9 |
| | 337.90 | 2863082 | 102.01 | |
| | 339.55 | 2907803 | 103.1 | |
| 16B with menthol | 327.52 | 2803639 | 103.06 | 101.6 |
| | 328.91 | 2757927 | 100.95 | |
| | 332.91 | 2783892 | 100.68 | |

The results indicate that under the tested conditions there is no interference of nicotinamide signal with the signal of flumazenil. Accordingly, the aforementioned HPLC parameters are appropriate for evaluating the content of flumazenil in formulations comprising the flumazenil nicotinamide complex of the invention.

Example 5

HCl Acid Addition Salt of Flumazenil

Flumazenil chloride salt consisting of flumazenil and hydrochloride acid was prepared (FIG. 1). The increased solubility of the flumazenil chloride salt enabled formulating a composition comprising flumazenil at a concentration of 0.66%. The concentration of flumazenil in that composition is higher by about one order of magnitude than the concentration of flumazenil in the commercial product Romazicon® (Romazicon® contains 0.01% flumazenil).

Example 6

Stability Analysis

The short term stability (STS) of flumzenil-nicotinamide formulations was tested on two flumazenil solutions (Table 9).

TABLE 9

Formulations participated in the STS study (% w/w)

| Material | Batch No. 1 | Batch No. 2 |
|---|---|---|
| Flumazenil | 1 | 1.2 |
| Ethanol (absolute) | 40.1 | 40.1 |
| Propylene glycol | 10 | 10 |
| Citric acidic anhydrous | 0.05 | 0.05 |
| Niacinamide (nicotinamide) | 1.5 | 1.5 |
| Menthol | 0.1 | 0.1 |
| Water for injection | 47.2 | 47.0 |

The formulations were packed in 5-ml glass vials, capped with Teflon stoppers and crimped with aluminium seals. Vials were stored in a stability chamber at 25° C. and 40° C. Stability was evaluated at the following stability time points: 2 weeks, 1 months and 3 months. At each stability time point samples were tested for: pH, appearance and flumazenil assay.

The results are summarized in Table 10 below. The assay values for flumazenil were in the range of 90-110% and did not change over 3-months storage at 25° C. and at 40° C. The pH of the formulations remained in the range of 5.13-5.39 throughout the experiment (3 months) under all temperatures. Furthermore, the solutions remained clear during storage in the stability chambers over the period and storage conditions that were tested. Thus, the results clearly indicate that the flumazenil-niacinamide formulations are stable and suitable for long shelf lives.

TABLE 10

STS study

| Time point | Storage Temperature | Batch No. | | | |
|---|---|---|---|---|---|
| | | 1 | | 2 | |
| | | API content | | | |
| | | 1% | | 1.2% | |
| | | 25° C. | 40° C. | 25° C. | 40° C. |
| T-0 | pH | 5.17 | | 5.20 | |
| | Assay (%) | 105.1 | | 107.9 | |
| | Appearance | clear | clear | clear | clear |
| T-2 weeks | pH | 5.24 | 5.26 | 5.30 | 5.34 |
| | Assay (%) | 100.6 | 102.2 | 100.3 | 102.2 |
| | Appearance | clear | clear | clear | clear |
| T-1 month | pH | 5.24 | 5.38 | 5.31 | 5.39 |
| | Assay (%) | 99.5 | 100.2 | 99.6 | 98.4 |
| | Appearance | clear | clear | clear | clear |
| T-3 months | pH | 5.13 | 5.13 | 5.28 | 5.25 |
| | Assay (%) | 103.0 | 102.7 | 102.9 | 103.4 |
| | Appearance | clear | clear | clear | clear |

Example 7

Toxicity Studies in Dogs

Toxicity of the flumazenil formulation of the invention is conducted in dogs. Four formulations are tested: vehicle (control), low dose, medium dose and higdose, according to the following study design:

TABLE 11

Toxicity study design

| Dose | Main Study | | Recovery | |
|---|---|---|---|---|
| | Male | Female | Male | Female |
| Vehicle | 3 | 3 | 2 | 2 |
| Low dose | 3 | 3 | 2 | 2 |
| Medium dose | 3 | 3 | 2 | 2 |
| High dose | 3 | 3 | 2 | 2 |

Flumazenil is administered once a day, sublingually. The dose is sprayed under the tongue and is held there for at lest 5 minutes prior to swallowing.

All animals fast overnight (approximately 12 hours) prior to dosing and at least 2 hours postdose. Animals are observed twice daily and undergo detailed clinical observation weekly. The weekly observation include evaluating body weights and food consumption. Prior to initiation of the experiment, animals undergo physical examinations by staff veterinarian.

All animals pretest and at termination and recovery undergo ophthalmology evaluation. In addition, animal undergo electrocardiograms pretest, predose and postdose on day 1, predose and postdose prior to the terminal necropsy, and prior to the recovery necropsy.

Clinical pathology (hematology, coagulation, clinical chemistry and urinalysis) is obtained for animals pretest, and all survivors prior to the terminal and recovery necropsies. The tests are listed in Table 12 below.

Blood toxicokinetics is performed on blood samples collected on days 1 and 28 at six time points from each animal. Following necropsy, at the end of the experiment, weights of the following organs is measured: adrenals, brain, heart, kidneys, liver, lungs, ovaries with oviducts, pituitary, prostate, salivary glands, spleen, thyroid with parathyroid, thymus, testes and uterus. For all main study animals, a full set of standard tissues for slide preparation/microscopic pathology is collected (approximately 70). The target organs in recovery animals include gross lesions. A complete list of the target organs is given in Table 13 below. For toxicokinetic modeling standard parameters are evaluated, for example, AUC, $t_{1/2}$, Tmax and Cmax. Data is analyzed by standard statistical analysis.

TABLE 12

Standard clinical pathology tests

Standard hematology parameters evaluated

| | |
|---|---|
| Absolute and percent reticulocytes | Mean corpuscular hemoglobin |
| Erythrocyte count | Mean corpuscular hemoglobin concentration |
| Hematocrit | Mean corpuscular volume |
| Hemoglobin | Platelet count |
| Leukocyte count (total and differential) | Reticulocytes |

Standard coagulation parameters evaluated

| | |
|---|---|
| Prothrombin time | Activated partial thromboplastin time |

Standard clinical chemistry parameters evaluated

| | |
|---|---|
| Albumin/Globulin Ratio (calculated) | Glucose |
| Alanine aminotransferase | Phosphorus |
| Albumin | Potassium |
| Alkaline phosphatase | Sodium |
| Aspartate aminotransferase | Sorbitol dehydrogenase |
| Calcium | Total bilirubin (with direct if total exceeds1 mg/dL) |
| Chloride | Total cholesterol |
| Creatinine | Total protein |
| Gamma glutamyl transferase | Triglycerides |
| Globulin (calculated) | Urea nitrogen |

Standard urinalysis parameters evaluated

| | |
|---|---|
| Bilirubin | pH |
| Color and appearance | Protein |
| Glucose | Specific gravity |
| Ketones | Total volume |
| Microscopy of spun deposit | Urobilinogen |
| Occult blood | |

TABLE 13

Standard microscopic tissue list

Standard microscopic pathology for dogs

| | |
|---|---|
| Adrenal gland | Pancreases |
| Aorta | Pituitary |
| Bone with bone marrow, femur | Parathyroid gland |
| Bone with bone marrow, sternum | Prostate |
| Bone with bone marrow, rib | Salivary gland, mandibular |
| Bone marrow smear | Salivary gland, parotid |
| Brain | Salivary gland, sublingual |
| Epididymis | Skeletal muscle, biceps femoris |
| Esophagus | Skin |
| Eye (with optic nerve) | Small intestine, duodenum |
| Gallbladder | Small intestine, ileum with Peyers patches |
| Heart | Small intestine, jejunum |
| Joint, tibiofemoral | Spinal cord, cervical |
| Kidney | Spinal cord, lumbar |
| Large intestine, cecum | Spinal cord, thoracic |
| Large intestine, colon | Spleen |
| Large intestine, rectum | Stomach, cardia |
| Larynx | Stomach, fundus |
| Liver | Stomach, pylorus |
| Lung | Testis |
| Lymph node (mandibular) | Thymus |
| Lymph node (mesenteric) | Thyroid gland |

TABLE 13-continued

Standard microscopic tissue list

Standard microscopic pathology for dogs

| | |
|---|---|
| Lymph node (tracheobronchial) | Tongue |
| Lymph node (regional, if applicable) | Trachea |
| Mammary gland (process females only) | Urinary bladder |
| Nerve (sciatic) | Uterus with cervix |
| Nictitans gland | Vagina |
| Ovary | Gross lesions |
| Oviducts | Tissue masses |

Example 8

Reversal of Diazepam-Induced Sedative-Hypnotic Effects in Rats

The effect of flumazenil nicotinamide formulation A (Table 15) on reversal of diazepam induced sedative-hypnotic state was studied in SD rat model. The study end point was set by determining the sleeping time of the rats (females, 8-9 weeks of age, n=8) in each group. The experiment was conducted in two groups, of four rats each:

TABLE 14

Treatment groups

| Group No. | N= | Treatment |
|---|---|---|
| 1F | 4 | Flumazenil Formulation A |
| 2F | 4 | Placebo (vehicle) |

Following acclimation (5 days) inductive of sedative-hypnotic effects was induced by an intravenous injection of 20 mg/kg of benzodiazepine diazepam (Assival®) using a 24 G sized needle over approximately 15 seconds. In case an animal was not sufficiently sedated an additional injection of 5 mg/kg was administrated. The day of induction is defined as "Day 1".

The test item (Formulation A or placebo) was administered via the sublingual route twice at an interval of approximately 2 minutes once the animal had no righting reflex about 5 minutes post the second injection of the diazepam.

The components of the placebo solution are listed in Table 15.

TABLE 15

Placebo and flumazenil solutions for sublingual administration in rats.

| Component | Formulation A | Placebo |
|---|---|---|
| | % w/w | |
| Flumazenil | 1.1 | — |
| Ethanol | 40 | 10 |
| Propylene glycol | 10 | 20 |
| 30% HPCD in citric buffer 10 mM pH 4.0 | | 59.3 |
| Menthol in EtOH (1/1 w/w) | — | 0.1 |
| Propylparaben/Methylparaben in EtOH 0.02/0.18/10 w/w/w | — | 10.2 |
| Citric acid anyhdrous | 0.05 | — |
| Sodium citrate dehydrate | 0.05 | — |
| Nicotinamide | 1.5 | — |
| L-menthol | 0.1 | — |
| Water | 47 | — |

Sleeping Time Determination was carried out as follows: upon diazepam injection the animal was placed on its back in a bedded standard cage. Sleeping time was determined when the test animal was no longer capable to maintain its Righting Reflex. This reflex is defined as the animal's failure of righting 2 times within 30 seconds. Clock time was recorded after the first administration of the test item and again when the animal woke up. The sleeping time was determined as the elapsed time between first administration of the tested item and the time that the animal regained its Righting Reflex. The entire study was recorded (VCR).

Figure 5:
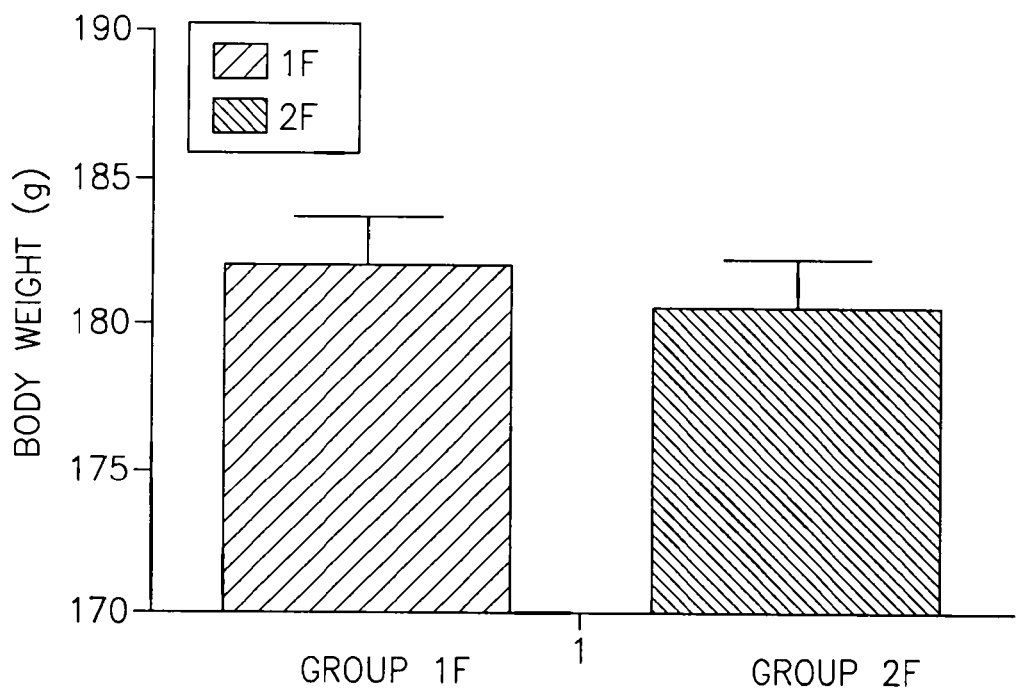
FIG. 5 presents the body weight distribution of the rats (1F-treatment and 2F-placebo) in the study of reversal diazepam-induced sedative-hypnotic effects.
Figure 6:
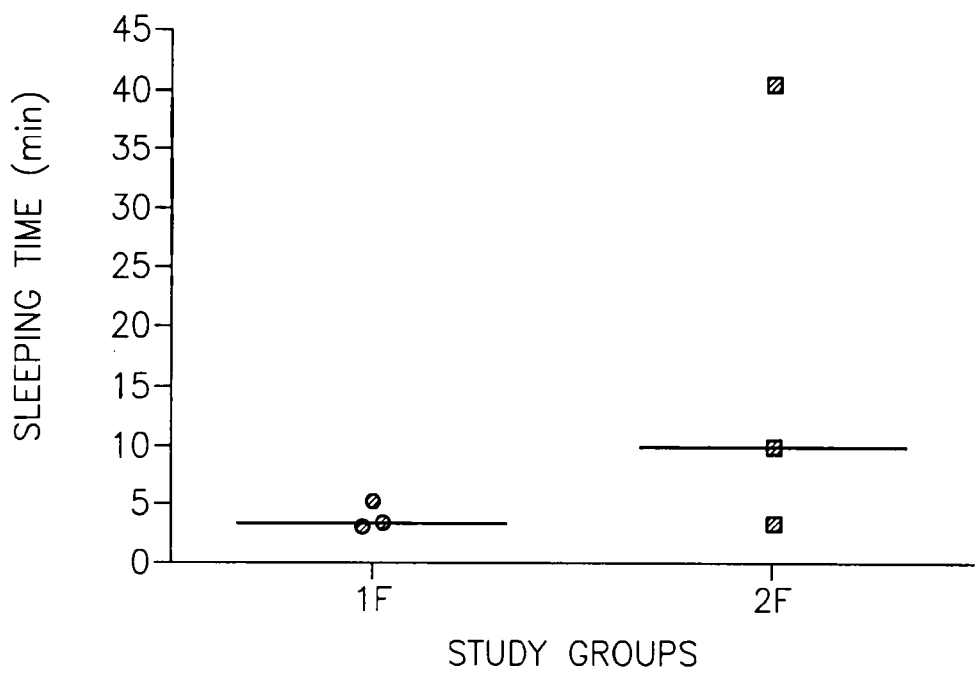
FIG. 6 exhibits the sleeping time of the rats (1F-treatment and 2F-placebo) following treatment.

Observations for signs of morbidity and mortality were performed twice a day. One animal died immediately after diazepam dosing. Individual body weight determination was made on Day 1 prior to induction (see Table 16 and FIG. 5). At study termination all animals were euthanized by respiratory exposure to excess $CO_2$.

TABLE 16

Body weights

| Group | Animal No. | Body weight (g) | Group | Animal No. | Body weight (g) |
|---|---|---|---|---|---|
| 1F | 1 | 183 | 2F | 5 | 184 |
| | 2 | 187 | | 6 | 175 |
| | | | | 7 | 181 |
| | 4 | 178 | | 8 | 182 |
| Average ± sd | | 182 ± 3.3 | Average ± sd | | 180.5 ± 3.3 |

As shown in Table 17, sleeping time following drug treatment was clearly shortened. The large variation is due to the small number of animals in the two groups.

TABLE 17

Sleeping time

| Group | Animal No. | Time (min) | Group | Animal No. | Time (min) |
|---|---|---|---|---|---|
| 1F | 1 | 3.18 | 2F | 5 | 40.46 |
| | 2 | 5.24 | | 6 | 10.1 |
| | — | — | | 7 | 3.5 |
| | 4 | 3.45 | | 8 | died |
| Average ± sd | | 3.96 ± 0.91 | Average ± sd | | 18.02 ± 16.02 |

Example 9

Clinical Study Protocols

PK Protocol

The primary objective is to determine the single dose absolute bioavailability of sublingual (SL) Formulation A using the marketed IV flumazenil formulation as the comparator. The secondary objectives are to characterize the concentration time course of two dose levels of SL Formulation A to support dose selection for Phase 2 and 3 studies and to evaluate the safety and tolerability of flumazenil formulations.

Study design includes masking and enrolment, open label, randomized, three-way crossover study, with 15 healthy subjects ≥18 years of age, with no medication, based on the following study arms:

1. SL Formulation A 100 µl (1.1 mg) N=5
2. SL Formulation A 200 µl (2.2 mg) N=5
3. IV Flumazenil (Romazicon®) (0.2 mg) N=5

Study conditions: standardized as much as possible in terms of die and fluid intake. This type of study is interventional. The secondary outcome measure is to examine the safety and tolerability of Formulation A (1.1 mg and 2.2 mg), where the safety endpoints include: adverse event monitoring, vital signs, physical examinations, clinical laboratory tests and ECGs.

The time-points for blood and serum tests of flumazenil concentration are:

0, 10 min, 30 min, 60 min, 90 min, 2 h, 4 h, 6 h and 24 h. PK parameters for analysis are Cmax, Tmax, Cmin, T min, $AUC0-\infty$, $AUC_0\text{-}t$ and $T_{1/2}$.

Phase 2B Study: Dose Range Study of SL Flumazenil

The study is a Phase 2B Dose Range, Efficacy and Safety of sublingual Formulation A for the indication: reversal of the residual effects of GABA related (benzodiazepine (BNZ) and nonBNZ) hypnotic drugs in insomniac patients. The residual sedative effect relates to benzodiazepine (BNZ) and nonBNZ hypnotic drugs. The study evaluates different doses of Formulation A in comparison to a placebo. Formulation A is provided as a sublingual (SL) spray formulation with flumazenil 11 mg/ml.

Short-term safety and tolerability data is monitored along with psychomotor/cognitive and behavioral effects. The rationale of this study is to support study the pivotal efficacy phase 3 study, for the aforementioned indication.

Doses are determined with reference to the bioavailability study results. The study includes two groups of insomniac patients (males and females) aged ≥18 y, Group A (n=60) and Group B (n=60). Each group is divided into Dose 1 (n=20), Dose 2 (n=20) and Placebo (n=20). The subjects all groups (n=20) are tested for the safety and efficacy of SL spray administration of Formulation A in the reversal of the sedative residual effect of BNZ (Group A) or Non BNZ (Group B).

Response to treatment is evaluated for each treatment arm. Good Response (GR) is R*25%, namely, an improvement of 25% in efficacy parameters of Formulation A treated patients compared to placebo/baseline. Very Good Response to treatment (VGR) is R*35%. The secondary objectives are to evaluate the duration of action of a single dose of SL CRLS003 and to evaluate the safety of a single daily dose of Formulation A for 7 days. Study Design is randomized, double blind, dose range and placebo controlled.

The following examinations are carried out:
a. Physical examination, clinical laboratory, vital signs.
b. Sleep induction by BNZ/nonBNZ (Study A/B, respectively), per patient routine.
c. All patients undergo full polysomnography.
d. At 6 AM patients are awaked.
e. Baseline—On awakening digit symbol substitution test (DSST) is performed.
f. Patients are randomly treated with Formulation A 1.1 or 2.2 mg or with placebo.
g. The following tests are conducted at 10 min, 60 min, and 120 min following SL Formulation A or placebo administration: DSST, immediate Word Recall Test (iWRT), Visual Analog Scale (VAS) and Profile of Mood States (POMS).
h. Patients will be self-treated throughout the week at home using daily hypnotics and Formulation A/placebo (blinded) on awakening. Patients will answer questions and write sleep and performance logs.
i. On the 7th night, patients will report to the clinic for full polysomnography and will repeat the same evaluation as in the previous visit.
j. One week after termination, subjects will visit for safety monitoring.

Subjects meet all of the following inclusion criteria:
a. Each subject understands and voluntarily signs an informed consent form prior to any study-mandated procedure.
b. Male or female aged ≥18 y at screening. Women of childbearing potential must have a negative pregnancy test at the screening visit and use a reliable method of contraception during the entire study duration (e.g., contraceptive pill; intra-uterine device; contraceptive injection (prolonged-release gestagen); subdermal implantation; vaginal ring or transdermal patch).
c. Body mass index ≥18.5 and <32 $kg/m^2$.
d. Chronic insomniac who are regularly treated by BNZ (Group A) or nonBNZ (Group B) for at least 2 months and report residual morning symptoms.
e. Each subject is in good health as determined by a medical history, physical examination and ECG.
f. Negative regarding any use of illicit drug, alcohol (ethanol), stimulants.

Exclusion criteria are:
1. Using medications, except hypnotics and contraceptives, 1 month prior to screening.
2. A change in the hypnotics within the last 2 months.
3. Any sleep associated complains other than insomnia
4. History of Epilepsy and or anti-epileptic drugs.
5. Excessive caffeine consumption (≥500 mg per day).
6. Pregnancy or breast feeding.
7. Night shift workers within 1 month prior to the screening visit.
8. Clinically relevant ECG abnormalities.
9. History of alcohol or drug abuse within 3 years prior to the screening visit.
10. Cognitive Behavioral Therapy (CBT) started within 1 month prior to screening.
11. Known hypersensitivity to drugs of the same class as the study treatment, or any excipients of the drug formulation.
12. Treatment with another investigational drug within 1 month prior to the screening.
13. History of severe head injury.

The study includes the following visits:

Visit 1—Screening visit: A signed and dated informed consent form is collected from each participating subject, prior to any screening procedures. Screening visit takes place up to 14 days prior to treatment visit. Subjects who are screened are assigned a 3-digit Screening number. During the screening visit, the following procedures are performed: Review Inclusion/Exclusion criteria; Medical history inquiry and demographic data; Record prior medication; Neurological assessment; Conduct physical examination including vital signs, height and weight measurements; Pregnancy test; 12-lead electrocardiography.

Visits 2 and 3—Treatment at sleep laboratory visits: prior to Formulation A administration subjects undergo full physical examination, including sublingual and oral examination; vital signs measurements; adverse events and concomitant medication inquiry; Blood baseline tests. After determining that a subject is eligible, subjects receives a Randomization number and progresses to the sleep induction stage. At this stage the subject receives a sleep/hypnotic drug as follows:

Study A: BNZ (same drug and dose that patients use regularly)

Study B: nonBNZ (same drug and dose that patients use regularly)

Subjects sleep under full polysomnography until 6 AM. On awakening DSST is performed and the study Drug is administered: (At time 0) 0.1/0.2 ml Formulation A or placebo (randomly and blindly). Thereafter, at 10 min., 60 min., and 120 min. post Formulation A administration, subjects are tested for psychomotor performance and behavioral tasks and vital signs. Safety measurement are conducted after performance tasks completion, as follows, full physical examination, including the sublingual and the oral cavity testing; neurological assessment; vital signs measurements; AE inquiry and blood tests.

The participants are released by a physician and are not allowed to drive until 10 hours after hypnotic administration. On the 7th day after study visit 2, visit 3 is conducted applying same procedures as in visit plan 2.

Across the study at home, patients continue using hypnotics and, on awakening taking Formulation A. Patients also keep a daily sleep-wake-performance log. The following prohibitions apply to the visits: caffeine consumption after 2:00 pm on the day before any study visit; consumption of alcohol or grapefruit (including as juice) from the day prior to each of the study visits, and for 3 consecutive days; and napping on the day before any study visit. During study any diet or non-pharmacological activity are allowed if started at least 1 month prior to the screening visit and stable until 24 hours after the last administration of study treatment.

Follow-up visit—Subjects pay a safety visit at day 7 after treatment termination and are examined, including blood tests, and report adverse effects (AEs).

Unscheduled visit—Subjects are monitored for AEs throughout the study. For any reported AEs defined as "Moderate or "Severe", the subject is instructed to visit the clinic for safety measures as required. Causal AEs is monitored until resolved.

Study Duration: subjects participate in this study for 1 week of therapy and 1 week of follow-up. Interim analysis is carried (after 30 patients). Standard statistical methods are used to analyze the results (e.g. mean and standard deviation based on student-t test and ANOVA), where $p<0.05$ defines significance.

Phase 3 Pivotal Efficacy Study

This study is a double blind evaluation of SL Formulation A for reversal of next day residual sedative effect from hypnotic drugs used to treat insomnia. It is directed to evaluate the safety and effectiveness of SL Formulation A in insomniac patients in reversing the next day residual effect of hypnotic drugs. The study is designed to collect short-term safety and tolerability data along with psychomotor/cognitive and behavioral function. It is an interventional type of study. The indication, drugs and treatment are similar to the those tested in the Phase 2B study.

Sample includes 300 subjects (150 per treatment group) randomized to flumazenil or placebo 1:1 ratio, stratified by BNZ or nonBNZ. Treatment response is evaluated for each treatment arm. Good Response (GR) is R*25%. Secondary objective include safety of SL Formulation A compared to placebo administered daily for 6 weeks. The Study Design is randomized, double blind, placebo and controlled.

All subjects are evaluated for the safety and efficacy of SL Formulation A to reverse the sedative effect of BNZ or nonBNZ applying the same routine used in Phase 2B study with the following exceptions:
 i. Patients are self-treated for 3 weeks using daily hypnotics and Formulation A/placebo (blinded) on awakening.
 ii. By the end of the 3rd week ±3 nights and at the last night (6 weeks after trial start), patients visit the clinic for full polysomnography and repeat the procedures and testing described above.
 iii. Two weeks after the last treatment, the patient take safety monitoring and AE inquiry.

Subjects eligible for the study meet all of the aforementioned inclusion and exclusion criteria. The study includes the same type of visits listed above, with the addition of a fourth sleep laboratory visit.

Phase 3 Double Blind Placebo Controlled Trial for the Evaluation of Formulation a in the Treatment of Episodic Hepatic Encephalopathy (HE) Grade $\geq 2$.

The purpose of this study is to evaluate mental score/quality of life improvement in patients with episodic HE following the administration of sublingual flumazenil (Formulation A). This is an interventional type of study. The indication is: relief of cognitive impairment symptoms in patients with episodic HE. The investigational drug is Formulation A sublingual spray comprising 1.12 mg/ml Flumazenil. The time to recovery from episodic HE grade $\geq 2$ is defined as a decrease of Conn score to Grade <2, or a decrease in Asterixis.

The secondary objectives of this study are as follows:
 a. Duration and number of HE-related hospitalization.
 b. Time to any increase from baseline in Conn score.
 c. Time to any increase from baseline in Asterixis grade
 d. Number connection Test (NCT or Reitan Test)
 e. Continuous reaction times to sound (CRT)
 f. Block design test (BDT)
 g. Symbol digit modalities test (SDMT)
 h. Mean change from baseline in fatigue domain score on the Chronic Liver Disease Questionnaire (CLDQ)

The study design is randomized, placebo controlled, double blinded administered sublingual flumazenil twice a day for 3 weeks. During study, patients with episodic HE grade $\geq 2$ are screened for a respond to flumazenil therapy. Baseline assessment includes in addition to the routine testing described below: Clinical assessment (physical and blood tests), EEG, plasma assays for benzodiazepines and NCT.

Physical and blood tests include:
 a. Ammonia measurements, weight, renal functions electrolytes each visit.
 b. EEG
 c. A questionnaire regarding diarrhea and abdominal discomfort
 d. Cognitive impairment
 e. Performance memory test each visit (e.g. NCT and Reitan Test)
 f. Quality of life evaluation (HE related hospitalization). Conn score and asterixis increase are documented.

The study population includes male and female, cirrhotic patients aged $\geq 18$ y, with episodic HE grade $\geq 2$.

Inclusion criteria that subjects eligible for enrolment into the study meet are:
 a. Episodic HE grade $\geq 2$.
 b. Responsiveness to flumazenil therapy.
 c. Each subject understands and voluntarily signs an informed consent form prior to any study-mandated procedure.
 d. Male or female aged $\geq 18$ at screening.
 e. Women of childbearing potential must have a negative pregnancy test at the screening visit and use a reliable method of contraception during the entire study duration (e.g. Contraceptive pill; Intra-uterine device; Contraceptive injection (prolonged-release gestagen); Subdermal implantation; Vaginal ring or Transdermal patch).

Exclusion criteria include chronic BNZ therapy and epilepsy.

Safety assessment is based on changes from screening/baseline for clinical AEs reported by the subject, or observed by the investigator assessed by physical exam, oral and sublingual assessment, neurological assessment and vital signs.

Standard statistical methods are used to analyze the results (e.g. mean and standard deviation based on student-t test and ANOVA), where $p<0.05$ defines significance.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A pharmaceutically acceptable complex of ethyl 8-fluoro-5,6-dihydro-5-methyl-6-oxo-4H-imidazo[1,5-a][1,4]benzodiazepine-3-carboxylate (flumanzenil) or a salt thereof and a complexation agent or a derivative thereof, wherein the complexation agent is selected from the group consisting of: nicotinamide, sodium nicotinate, sodium benzoate, sodium hydroxybenzoates, sodium salicylate, sodium gentisate, gentisic acid ethanolamide, sodium toluates, sodium aminobenzoate, sodium anthranilate, sodium butylmonoglycolsulfate and resorcinol.

2. The pharmaceutically acceptable complex of claim 1, wherein the complexation agent is nicotinamide or a derivative thereof.

3. The pharmaceutically acceptable complex of claim 1, wherein the complexation agent:flumazenil ratio is in the range of 1:1 to 2:1.

4. The pharmaceutically acceptable complex of claim 1, wherein the pharmaceutically acceptable complex is a flumazenil nicotinamide complex.

5. A pharmaceutical composition comprising the flumazenil complex of claim 4 and a pharmaceutical acceptable carrier.

6. The pharmaceutical composition of claim 5, wherein the composition is in a form selected from the group consisting of: a pill, tablet, lozenge, coated tablet, granule, capsule, hard or soft gelatin capsule, aqueous solution, alcoholic solution, oily solution, syrup, emulsion suspension pastille suppository, solution for injection or infusion, ointment, tincture, cream, lotion, powder, spray, transdermal therapeutic systems, nasal spray, aerosol mixture, microcapsule, implant, rod and plaster.

7. The pharmaceutical composition of claim 5, wherein the composition is in a form selected from the group consisting of: immediate release, delayed release, pulsatile release, continuous release and repetitive release.

8. The pharmaceutical composition of claim 5, wherein the concentration of flumazenil is within the range of about 0.4 to 2% w/w.

9. The pharmaceutical composition of claim 8, wherein the concentration of flumazenil is within the range of about 0.5 to 1.8% w/w.

10. The pharmaceutical composition of claim 5, further comprising a solubilizing agent selected from an alcohol, a glycol and a combination thereof.

11. The pharmaceutical composition of claim 10, wherein the solubilizing agent comprises a combination of an alcohol and a glycol and wherein the alcohol:glycol ratio is at least 1.5:1.

12. The pharmaceutical composition of claim 11, wherein the alcohol:glycol ratio is in the range of 1.5:1 to 5:1.

13. The pharmaceutical composition of claim 10, wherein the solubilizing agent comprises a combination of an alcohol and a glycol and wherein the concentration of the solubilizing agent is at least 40%.

14. The pharmaceutical composition of claim 13, wherein the concentration of the solubilizing agent is in the range of 40% to 60%.

15. The pharmaceutical composition of claim 10, further comprising a buffering agent.

16. The pharmaceutical composition of claim 10, further comprising at least one agent selected from the group consisting of: a penetration enhancer, a surfactant and cyclodextrin.

17. The pharmaceutical composition of claim 10, further comprising a preservative selected from the group consisting of: benzyl alcohol, propylparaben, methylparaben and combinations thereof.

18. The pharmaceutical composition of claim 16, wherein the penetration enhancer is menthol.

19. The pharmaceutical composition of claim 15, wherein the buffering agent is selected from the group consisting of: citric buffer, sodium chloride and combination thereof.

20. The pharmaceutical composition of claim 16, wherein the surfactant is benzalkonium chloride.

* * * * *